United States Patent
Gordon et al.

(10) Patent No.: US 10,981,948 B2
(45) Date of Patent: Apr. 20, 2021

(54) PROCESSES FOR INCREASING PLANT PROTEIN YIELD FROM BIOMASS

(71) Applicant: Cavitation Technologies, Inc., Chatsworth, CA (US)

(72) Inventors: Roman Gordon, Studio City, CA (US); Igor Gorodnitsky, Marina del Rey, CA (US); Naum Voloshin, Los Angeles, CA (US); Maxim A. Promtov, Tambov (RU)

(73) Assignee: Cavitation Technologies, Inc., Chatsworth, CA (US)

( * ) Notice: Subject to any disclaimer, the term of this patent is extended or adjusted under 35 U.S.C. 154(b) by 0 days.

(21) Appl. No.: 17/024,547

(22) Filed: Sep. 17, 2020

(65) Prior Publication Data

US 2021/0002326 A1 Jan. 7, 2021

Related U.S. Application Data

(63) Continuation-in-part of application No. 16/664,559, filed on Oct. 25, 2019, which is a continuation-in-part of application No. 15/375,809, filed on Dec. 12, 2016, now Pat. No. 10,507,442.

(51) Int. Cl.
*C07K 1/00* (2006.01)
*C07K 1/14* (2006.01)

(52) U.S. Cl.
CPC .................. *C07K 1/145* (2013.01)

(58) Field of Classification Search
CPC ......... C07K 1/145; C01K 1/14; B01F 5/0688; B01F 2215/0036; B01F 2215/0014
See application file for complete search history.

(56) References Cited

U.S. PATENT DOCUMENTS

| | | | |
|---|---|---|---|
| 1,727,753 | A | 9/1929 | de Bethune |
| 2,092,992 | A | 9/1937 | Thalman |
| 2,734,728 | A | 2/1956 | Myers |
| 2,893,846 | A | 7/1959 | Wistrich et al. |

(Continued)

OTHER PUBLICATIONS

Roohinejad ("Negative pressure cavitation extraction: A novel method for extraction of food bioactive compounds from plant materials" (Year: 2016).*

(Continued)

*Primary Examiner* — Anshu Bhatia
(74) *Attorney, Agent, or Firm* — Kelly & Kelley, LLP

(57) ABSTRACT

A process for increasing protein yield from biomass (beans, oilseeds, cereals, nuts, rice, soybeans, bran, etc.), as well as, for reducing the amount of chemical and biological reagents used in the process, involves application of multiple hydrodynamic cavitation treatments of a biomass suspension or other combination of biomass with solvents and reagents—in the preparation, extraction, and processing or the biomass and proteins. The biomass suspension is preferably subjected to at least three cavitation treatments in order to facilitate the crushing of biomass, splitting of fibers, and rupture of cell membranes, thereby increasing the mass transfer surface area and intensifying the extraction of protein and lipids. At the stage of washing and neutralization the protein solution may be subjected to a fourth cavitation treatment to obtain the purified protein.

20 Claims, 11 Drawing Sheets

(56) References Cited

U.S. PATENT DOCUMENTS

| | | | |
|---|---|---|---|
| 3,013,780 | A | 12/1961 | Wistrich |
| 4,018,755 | A * | 4/1977 | Wang ................. A23J 1/14 530/378 |
| 4,869,849 | A | 9/1989 | Hirose et al. |
| 5,810,474 | A | 9/1998 | Hidalgo |
| 7,892,579 | B2 | 2/2011 | Cao |
| 2011/0268852 | A1 | 11/2011 | Martini et al. |
| 2014/0105856 | A1* | 4/2014 | Schendel ............ A61K 35/28 424/85.2 |

OTHER PUBLICATIONS

Lianzhou Jiang et al.; Effects of ultrasound on the structure and physical properties of black bean protein isolates; Elsevier; Food Research International 62 (2014); pp. 595-601.

Xue Yang et al.; Effects of ultrasound pretreatment with different frequencies and working modes on the enzymolysis and the structure charaterization of rice protein; Elsevier; Ultrasonics Sonochemistry 38 (2017); pp. 19-28.

K.E. Preece et al.; Intensification of protein extraction from soybean processing materials using hydrodynamic cavitation; Elsevier; Innovative Food Science and Emerging Technologies 41 (2017) pp. 47-55.

Mudasir Ahmad Malik et al.; High intensity ultrasound treatment of protein isolate extracted from dephenolized sunflower meal: Effect on physicochemical and functional properties; Elsevier; Ultrasonics—Sonochemistry 39 (2017); pp. 511-519.

K.E. Preece et al.; Pilot-scale ultrasound-assisted extraction of protein from soybean processing materials shows it is not recommended for industrial usage; Elsevier; Journal of Food Engineering 206 (2017); p. 1-12.

Hua Yang et al.; The extraction of collagen protein from pigskin; Journal of Chemical and Pharmaceutical Research (2014); pp. 683-687.

Cunshan Zhou et al. Ultrasonics Sonochemistry, 2013; Lianzhou Jiang et al. Food Research International, 2014; Xue Yang et al. Ultrasonics Sonochemistry, 2017; Mudasir Ahmad Malik et al. Ultrasonics—Sonochemistry, 2017; K.E. Preece et al. Journal of Food Engineering, 2017.

Alli I , Gibbs BF , Okoniewska MK , Konishi Y , Dumas F 1993. Identification and characterization of phaseolin polypeptides in a crystalline protein isolated from white kidney beans (*Phaseolus vulgaris*) . J Agric Food Chem 41 : 1830-1834.

Moholkar VS, Pandit AB. Modeling of hydrodynamic cavitation reactors: a unified approach. Chemical Engineering Science 2001; 56(21-22): 6295-6302. DOI:10.1016/S0009-2509(01)00253-6.

\* cited by examiner

PROCESSES FOR INCREASING PLANT PROTEIN YIELD FROM BIOMASS

RELATED APPLICATION

This application is a continuation-in-part of U.S. patent application Ser. No. 16/664,559, filed on Oct. 25, 2019.

FIELD OF THE INVENTION

The present invention is directed to a multi-stage process for increasing the yield of plant protein from biomass and reducing the amount of chemical and biological reagents used in the production of plant protein using hydrodynamic cavitation. In the present invention, hydrodynamic cavitation is used to treat heterogeneous fluid systems with a static mechanical device that creates cavitation in the fluid flow. Cavitation promotes the synthesis of intermediate and final products in total protein production. The method can also find applications in other areas of fluid handling and other industries.

BACKGROUND OF THE INVENTION

Plant protein may be derived from biological vegetable materials, i.e., biomass. Prior art processes derived plant proteins rom a number of sources, many of which are time consuming and/or cost intensive to produce or manufacture. The prior art processes for producing plant proteins would benefit greatly from an improved and more efficient method of producing.

The difficulty in isolating protein from plant material lies in the structural features of the plant cell. Its cell wall is multi-layered and therefore has high strength. By destroying the membrane, cellular protein can also be easily denatured, since it is particularly sensitive to the action of most chemicals and is easily destroyed by heating, distillation, and other procedures necessary for the purification of substances. Physical methods of processing plant materials are used to intensify the extraction process and increase the yield of plant protein from biomass. Many studies have established the beneficial effects of ultrasonic treatment of biomass to produce vegetable protein. Ultrasound technology, as a non-thermal physical processing technology, was widely applied in food industry, especially in extraction, enzymolysis, emulsification.

Ultrasound is commonly used to mix the suspension used in chemical processes to facilitate mass transfer of the solute and convection in liquids. Ultrasonication increased the destruction of internal hydrophobic interactions of protein molecules and accelerated protein molecular motion, which resulted in protein aggregation; unstable aggregates were violently broken up into smaller soluble protein aggregates by the forces of ultrasonication. However, the repolymerization of aggregates through noncovalent interactions occurred when treated with ultrasonication. Positive results in protein solubility and particle size reduction were achieved. Ultrasound improved protein extraction yield.

Ultrasound treatment can also improve enzymatic hydrolysis. Ultrasonication applied during chemical reactions can be used to modify the proteins or used as a pre-treatment, for direct modification of physicochemical properties of proteins for example solubility, turbidity, emulsification, particle size, thermal properties etc. During ultrasonic treatment, the structural and functional properties of proteins are changed due to alteration in their molecular characteristics. Ultrasonic treatment causes partial unfolding and reduces the intermolecular interactions of proteins, which is demonstrated by an increase in free sulfhydryl content and surface hydrophobicity, which leads to the improvement in solubility and fluid characteristics of protein dispersion (Cunshan Zhou et al. Ultrasonics Sonochemistry, 2013; Lianzhou Jiang et al. Food Research International, 2014; Xue Yang et al. Ultrasonics Sonochemistry, 2017; Mudasir Ahmad Malik et al. Ultrasonics—Sonochemistry, 2017; K. E. Preece et al. journal of Food Engineering, 2017).

There are known technologies and methods for extracting valuable substances from plant materials using ultrasound, for example, U.S. Pat. No. 7,892,579 and publication US2011/0268852, including obtaining protein from plant materials as disclosed in U.S. Pat. No. 4,018,755. In these disclosures, a suspension of plant materials made from pre-ground plant materials (seeds, beans, nuts, etc.) is subjected to ultrasonic treatment. As a result of ultrasonic treatment with the generation of cavitation, the protein is extracted from the biomass, which is then isolated from the suspension and dried.

Cavitation is defined as the generation, subsequent growth and ultimate collapse of vapor- or gas-filled cavities in liquids resulting in significant energy release. As understood in this broad sense, cavitation includes the familiar phenomenon of bubble formation when water is brought to a boil under constant pressure. In engineering and science, the term cavitation is used to describe the formation of vapor-filled cavities in the interior or on the solid boundaries created by a localized pressure reduction produced by the dynamic action of a liquid system. Cavitation generated by conventional stirring or acoustic waves requires more energy, has a longer residence time, and produces lesser yield than hydrodynamic cavitation as described below.

Accordingly, there is a need for a method to carry out heterogeneous mass transfer that does not require a large energy input. Furthermore, there is a need for an improve method of producing protein from biomass that is more efficient and more cost effective. The present invention fulfills these needs and provides further related advantages through the utilization of hydrodynamic flow-through cavitation and the chemical and physical process involved.

SUMMARY OF THE INVENTION

The method described herein does not require high energy input as the cavitation device is operationally static, meaning once the position of the adjacent plates is set, they will not be moved during flow-through processing. The apparatus simply requires a minimum input to operate a pump to generate fluid velocity and pressure, and to create cavitation in the flow towards the goal of creating new products.

A process for extracting proteins from plant biomass begins with preparing plant biomass for extraction of protein. The preparation includes cleaning, washing, drying, milling, dehulling, chopping, or grinding raw plant biomass to remove contaminants and reduce particle size. The prepared plant biomass is stored in a storage hopper or similar container. The stored plant biomass from the storage hopper is then combined with demineralized water, acid, alkali, salt, enzymes, or solvent in an agitation tank forming a biomass slurry. The biomass slurry is subjected to a hydrodynamic cavitation treatment—preferably at least two hydrodynamic cavitation treatments and at an inlet pump pressure of 50-1500 psi—to extract plant protein from the biomass slurry. After the cavitation treatment, the biomass slurry is separated into a protein extract and biomass waste in equipment including a centrifuge, a filter press, or a filter membrane. The pH value of the protein extract is then adjusted to an isoelectric point of the proteins in the plant biomass. The plant proteins are then precipitated from the protein extract while at the isoelectric point. Finally, the plant proteins are separated from the protein extract using additional separation equipment.

When the preparing step involves a wet grinding process, the process further includes subjecting the prepared plant biomass to a preliminary hydrodynamic cavitation treatment to assist in dispersion and splitting of plant fibers, breaking of cell membranes, and increasing available mass transfer surface of biomass. This is done prior to the step of storing the prepared plant biomass. In the preparing step, a preferred particle size for the prepared plant biomass is less than 5 mm in diameter.

In some instances, when the raw plant biomass has an oil or fat content greater than 10% to 15% weight of oil/fat to weight of biomass, the process further includes separating the oil or fat from the biomass. Specifically, the stored plant biomass is mixed with demineralized water, lipid solvent, or lipid enzymes in a tank forming a lipid-containing biomass slurry. The lipid-containing biomass slurry is subjected to an intermediate hydrodynamic cavitation treatment—preferably at least two intermediate hydrodynamic cavitation treatments and at an inlet pump pressure of 50-1500 psi—for breaking of cell membranes, fiber fluffing, and increasing penetration of solvent or enzymes. A lipid-protein emulsion is then extracted from the lipid-containing biomass slurry. The lipid-protein emulsion is then separated into a lipid fraction and a protein fraction in the separation equipment. The lipid-containing biomass slurry and the lipid fraction are transported to the agitation tank. The protein fraction is combined with the protein extract prior to the step of adjusting the pH value. The oil or fat content consists essentially of Fatty Acids, Glycerolipids, Glycerophospholipids, Sphingolipids, Sterols, Prenols, Saccharolipids, Polyketides, or a combination.

The process further includes combining the separated plant protein with demineralized water or chemical reagents in a protein agitation tank to form a protein wash mixture. The protein wash mixture is subjected to an additional hydrodynamic cavitation treatment to wash and neutralize the plant protein. The plant protein is separated from the protein wash mixture using additional separation equipment. The plant protein is dried for food grade protein production.

The plant biomass preferably consists essentially of beans, oilseeds, cereals, hemp, potatoes, camellia, alfalfa, amaranth, kiwi seeds, nuts, rice, soybeans, bran or a combination. The plant protein consists essentially of Glycoproteins, Lipoproteins, Metalloproteins, Nucleoproteins, Phosphoproteins, Chromoproteins or a combination. The enzymes preferably consist essentially of lipase enzymes or cellulase enzymes. The combining step may include introducing microbes or fungi that produce lipase enzymes or cellulase enzymes to the stored plant biomass. The microbes or fungi preferably consist essentially of *Escherichia Coli, Saccharomyces cerevisiae, Zymomonas mobilis, Lactobacillus buchneri*, or *Clostridium acetobutylicum*.

An alternate process for extracting proteins from plant biomass begins with preparing the plant biomass for extraction by mechanical grinding. A first biomass suspension is formed by combining the prepared plant biomass and water. The first biomass suspension is subjected to a first hydrodynamic cavitation treatment to disperse biomass particles, separate biomass fibers, and disrupt biomass cell membranes forming a processed biomass. A processed biomass suspension is then formed by combining the processed biomass with one or more of water, organic solvent, and enzymes. The processed biomass suspension is subjected to a second hydrodynamic cavitation treatment to extract proteins and lipids from the biomass, forming a biomass dispersion. The biomass dispersion is separated into a biomass solid waste flow and a lipid-protein emulsion. The lipid-protein emulsion is separated into a lipid fraction and a protein fraction. A second biomass suspension is formed by combining the biomass solid waste flow with one or more of water, acid, alkali, salts, solvent, or enzymes. The second biomass suspension is subjected to a third hydrodynamic cavitation treatment to extract proteins from the second biomass suspension forming a second protein fraction.

The protein fraction and the second protein fraction are combined to form a combined protein fraction. The proteins are precipitated out of the combined protein fraction forming a protein solution. The protein solution is then combined with one or more of water and reagents forming a prepared protein solution. The prepared protein solution is subjected to a fourth hydrodynamic cavitation treatment to facilitate separation of proteins from the prepared protein solution. The prepared protein solution is separated into a liquid solution and purified concentrated protein. The purified concentrated protein is then dried.

The biomass consists essentially of beans, oilseeds, cereals, hemp, potatoes, camellia, alfalfa, amaranth, kiwi seeds, nuts, rice, soybeans, bran or a combination. The step of forming the first biomass suspension includes mixing the prepared plant biomass with demineralized water in a ratio of 10% to 50% w/v. In the step of forming the second biomass suspension, the acid preferably consists of citric acid in a range of 1% to 5% v/v or sulfuric acid in a range of 1% to 5% v/v, and the alkali preferably consists of sodium hydroxide in a range of 1% to 5% v/v. In the steps of forming the processed biomass suspension and forming the second biomass suspension, the enzymes preferably consist of lipase enzymes or cellulase enzymes. The steps of forming the processed biomass suspension and forming the second biomass suspension may include introducing microbes or fungi that produce lipase enzymes or cellulase enzymes. The microbes or fungi preferably comprise *Escherichia Coli, Saccharomyces cerevisiae, Zymomonas mobilis, Lactobacillus buchneri*, or *Clostridium acetobutylicum*, further including the step of adjusting a pH of the processed biomass suspension and the second biomass suspension to a desired pH for the microbes or fungi.

The present invention is directed to a process for increasing protein yield from biomass and for reducing the amount of chemical and biological reagents used in the production of plant protein from biomass. The process of obtaining protein begins with the preparation of biomass. The raw materials are pre-cleaned and washed, and the wash water is removed. The washed and purified biomass is mixed with demineralized water, acid, or alkali, or salt or enzymes are added, depending on the type of raw material and technology, to form an extractant. Depending on the type of plant material, it is crushed on the appropriate equipment (Milling, Dehuling, Chopping or Grinding) and a biomass suspension is obtained. Biomass can include beans, oilseeds, cereals, hemp, potatoes, camellia, alfalfa, amaranth, kiwi seeds, nuts, rice, soybeans, bran.

To break down fibers, remove the skin from the surface of plant material, rupture cell membranes, the biomass suspension is subjected to first hydrodynamic cavitation treatment to obtain a homogeneous finely dispersed suspension. When using hydrodynamic cavitation treatment of plant raw materials, lesser amounts of chemical reagents (acids, alkalis, salts) or biological reagents (enzymes or microbes or fungi that release enzymes) are required to obtain the same amount of plant protein as compared to prior art processes of plant protein production without hydrodynamic cavitation treatment of biomass suspension.

If the raw material has high oil content, such as soybeans, then the oil should be removed by solvent recovery or an oil-in-water emulsion will result. To completely remove oil from plant material, the biomass suspension may be subjected to a second hydrodynamic cavitation treatment. The liquid phase is separated from the solid phase, and the liquid phase, containing a solution of proteins and oils, is sent to the oil separation process. The separated protein solution is then sent for further processing.

If the plant material has low oil content, the biomass suspension can be subjected to a third hydrodynamic cavitation treatment for a more complete separation of the protein from the plant material. Enzymes (e.g., lipases, cellulases) may be added during this process to breakdown fat and carbohydrate components to facilitate protein extraction. Then the biomass suspension is sent to centrifugation and/or filtration to separate the vegetable meal and obtain a protein solution. When using hydrodynamic cavitation treatment of the biomass suspension, it is preferably ground to a micro-scale particle size, which makes it possible to exclude the stage of centrifugation and/or filtration of the biomass suspension. In this case, membrane technologies are used to isolate the protein. Increased protein concentration and purification is achievable following membrane filtration, chromatography, pH solubilization/precipitation and salt extraction. In the production of plant protein using hydrodynamic cavitation treatment of biomass suspension, the service life of membranes increases, since a suspension with homogeneous small-sized particles practically does not clog the pores of the membrane during a long period of operation.

The next steps in the process include washing, neutralizing and spray drying the precipitate. To separate the protein from soluble sugars and oligosaccharides, the process uses a relatively high salt concentration to salt out the protein. The precipitated protein goes through a washing and diafiltration to remove excess salt. The protein from any given source is a heterogeneous mixture of different types of proteins.

The present invention is also directed to a process for washing and neutralizing the chemical reactive from protein solution. To wash the solution containing the protein and the chemical components, water and neutralizing agents are added. To increase the contact area and intensify the interaction of the reagents, the protein solution is subjected to hydrodynamic cavitation treatment. The use of hydrodynamic cavitation treatment in the process of washing and neutralizing a solution of plant protein makes it possible to reduce the amount of chemical reagents due to their more effective action and the degree of completion of chemical processes.

Common protein modification techniques include chemical modification, limited enzymatic hydrolysis, and Maillard-induced glycation. Chemical modification by phosphorylation, acylation, and alkylation is among the initial approaches to simultaneously improving functionality, such as solubility, water holding capacity, and emulsification abilities, while solving processing challenges.

Enzymatic hydrolysis is the most researched and most common approach used in the industry for protein modification intended to improve functionality and physiological benefits. Degree of hydrolysis (% DH) and enzyme choice dictate the functional properties of the produced protein hydrolysate by influencing protein structure and peptide profile. A limited extent of hydrolysis (i.e. low % DH) is particularly important for producing functionally enhanced ingredients, because it controls for both the loss in structure and release of bitter peptides associated with more extensive hydrolysis.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
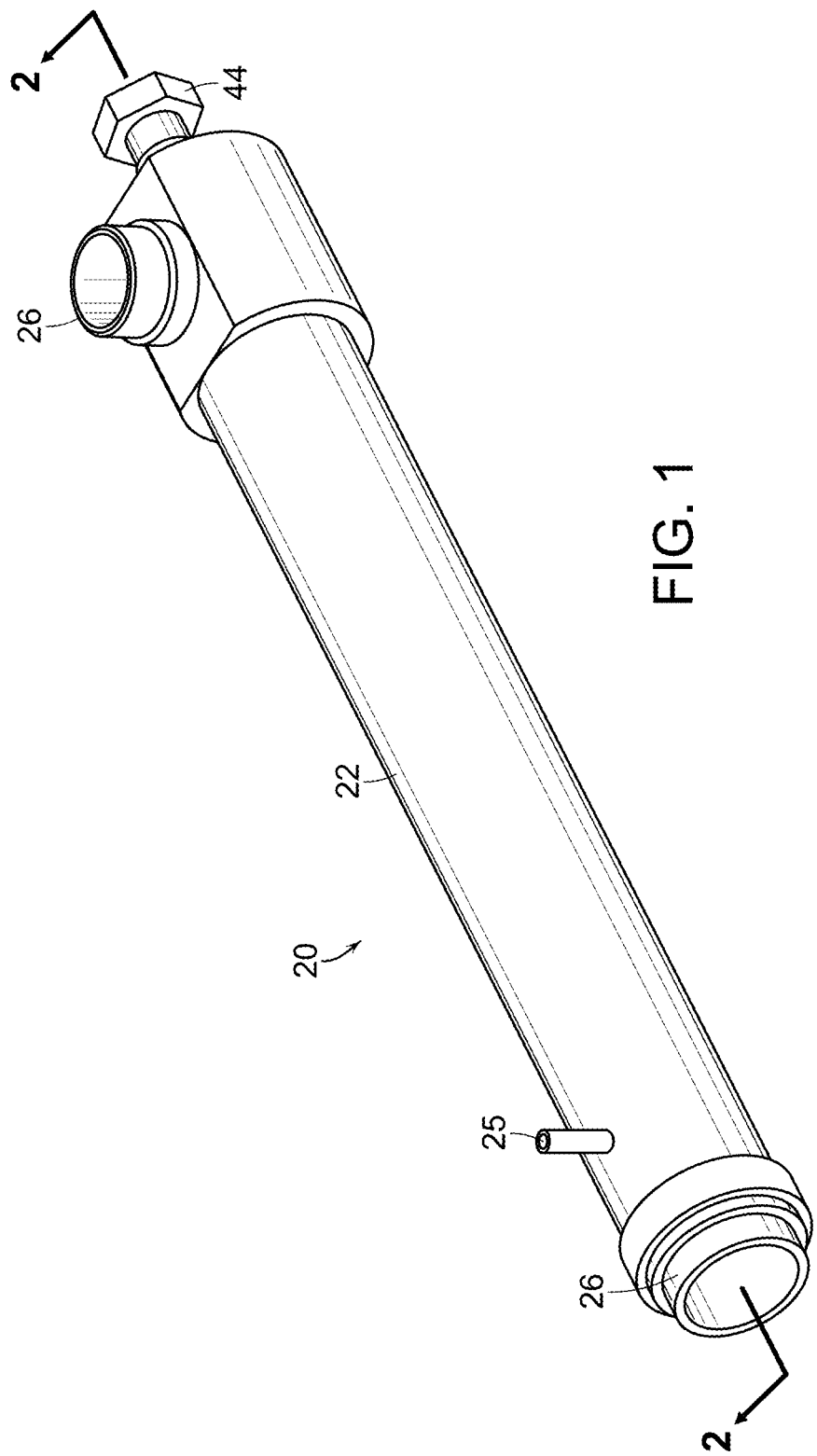
FIG. 1 is a perspective view depicting a preferred embodiment of a cavitation device for use in the process of the present invention.

The present invention is directed to a method and device for processing a fluidic reaction mixture via a hydrodynamic cavitation process with the result being the creation of new products. The reaction components inside the apparatus are influenced by pressure impulses and other features of controlled advanced hydrodynamic cavitation. The device and method herein described follows the aforementioned chemical reactions and processes such that the device stimulates cavitation in hydrodynamic liquids to the point where the end result is increased yield and quality of products.

A multi-step process for increasing protein yield from biomass using hydrodynamic cavitation is disclosed herein.

A process for reducing the amount of chemical and biological reagents used in the production of plant protein is also disclosed. More particularly, the multi-step process includes: (1) a process for the separation of oil from a biomass suspension using hydrodynamic cavitation; (2) a process for the extraction of protein from biomass using hydrodynamic cavitation; and (3) a process for washing and neutralizing chemical reactive compounds from protein solution using hydrodynamic cavitation.

The preferred hydrodynamic cavitation device described herein is highly versatile for the process for the separation of oil from biomass and the extraction of protein from plant biomass, which is an important and cost-intensive step in the production of plant protein, especially in prior art fermentation or biochemical processes.

Plants contain high amounts of fiber and cellulosic material that needs to be removed prior to protein extraction. Some plant materials are also high in fat or oil, making a separation step necessary prior to protein extraction. This is best accomplished by starting with a milling step. Examples of milling equipment used in industrial settings include centrifugal mills, hammer mills, ball mills, roller mills and disc attrition mills. De-hulling and milling can be done as a single unit operation or as two separate unit operations depending on the type of equipment used and the material being processed (i.e., ease of de-hulling). Effectively disintegrating plant materials by first hydrodynamic cavitation treatment to obtain micro particle sizes that allow for maximum fat and protein extraction is an important first step in processing.

Materials that have a fat or oil content that in the range of or greater than about 10% to 15% weight of fat/oil to weight of biomass, may require a defatting step. For example, soybeans seeds (17-23% w/w) are considered to have a high fat/oil content. The techniques most commonly used are solvent extraction using hexane, mechanical extraction and aqueous extraction. Both mechanical and solvent extraction techniques have their limitations.

As an alternative, aqueous techniques for fat extraction are being used by a second hydrodynamic cavitation treatment of the biomass suspension. In this case, after the first treatment the full fat biomass material is solubilized to perform a solid-liquid extraction/separation. During this step, insoluble compounds are removed, leaving a liquid solution containing both proteins and lipids. This solution is further separated by three-phase centrifugation to yield a solid, an aqueous and an oil/emulsion phase, each of which can be further processed downstream.

Enzymes (e.g., lipases, cellulases) may be added during this process to breakdown fat and carbohydrate components to facilitate protein extraction. The main principle of enzyme-assisted extraction is the use of enzymes which damage and/or degrade plant cell walls, so increasing the permeability of the oil in the oilseed. The two main approaches include the use of single and mixed enzymatic systems. The latter has increased utility, given that the mixed systems allow for various enzymes to simultaneously act on the cellular structures, leading to a more effective release of oil. The use of lipases or phospholipases to breakdown fats, in high fat aqueous extraction systems where emulsions are likely to occur, is particularly effective in combination with the hydrodynamic cavitation treatment.

Aqueous alkaline extraction is one of the most commonly used techniques for protein extraction. It takes advantage of the solubility of most proteins in alkaline pH solutions. In this process the prepared biomass, which may be full fat, partially defatted, or fully defatted, is processed in another hydrodynamic cavitation treatment, using water ratios ranging from 1:5 to 1:20. The occurrence of transient hydrodynamic cavitation in the mixture generates intense microturbulence that removes and refreshes the water in the close packed biomass matrix. The pH of the mixture is adjusted to alkaline (pH 8-11) and the mixture is treated in a cavitation reactor to maximize protein solubilization. The pH is maintained at the desired value and the temperature may be elevated (up to 55-65° C.) to further enhance protein solubilization and extraction. The mixture is subsequently filtered to remove any insoluble material to yield a supernatant containing the extracted proteins. Some extraction processes call for a second extraction of the precipitate using similar pH as in the first extraction or higher in order to extract any remaining proteins in the precipitate and increase protein recovery. The use of hydrodynamic cavitation treatment of biomass suspension during alkaline extraction makes it possible to reduce the amount of alkali in an aqueous solution due to crushing of the biomass particles and ensuring deep penetration of the aqueous-alkaline solution into the pores and capillaries of the plant raw materials for solubilization and protein extraction.

The solubility of some proteins increases under acidic conditions (i.e., pH<4). One example of such a protein is a bipyramidal crystalline protein preparation from seeds of white kidney bean (Alli I, Gibbs B F, Okoniewska M K, Konishi Y, Dumas F 1993. Identification and characterization of phaseolin polypeptides in a crystalline protein isolated from white kidney beans (*Phaseolus vulgaris*). J Agric Food Chem 41: 1830-1834). This low pH range can, therefore, be used to solubilize proteins prior to their recovery. The principle of acid extraction is similar to that of alkaline extraction, except that the initial protein extraction is conducted under acidic conditions. The acid extraction technique is generally used less frequently than the alkaline extraction technique and, as with alkaline extraction, processing conditions can influence the yield and purity of the finished product. The use of hydrodynamic cavitation treatment of biomass suspension during acid extraction makes it possible to reduce the amount of acid in an aqueous solution due to crushing of biomass particles and ensuring deep penetration of an aqueous solution of acid into the pores and capillaries of plant raw materials for solubilization and protein extraction.

Hydrodynamic cavitation in suspension causes intensive mixing of microvolumes of a liquid and particles of biomass. This contributes to the efficient removal of localized protein molecules formed in the biomass matrix. The selective extraction of proteins in aqueous solutions having different ionic strengths can be used for their fractionation and separation. The process is based on the salting-in and salting-out phenomenon of food proteins. At low molarities (0.5-1 M), ions of neutral salts promote the solubilization of proteins ("salting in"). Interactions between the ions and charges of proteins reduce electrostatic attractions between protein molecules enhancing their solubility. Additionally, the hydration of the ions increases the solvation of the proteins contributing to increased solubility. At higher salt concentrations (>1 M), competition between salts and proteins for available water forces the proteins to precipitate ("salting out"). After extraction, extensive dilution of the solution can cause these globulins to precipitate out of solution especially at low temperatures leading to their fractionation. The use of hydrodynamic cavitation treatment of biomass suspension during extraction with the use of salts makes it possible to reduce their amount in an aqueous solution due to crushing of biomass particles and ensuring deep penetration of an aqueous salt solution into the pores and capillaries of plant raw materials for solubilization and protein extraction.

Most proteins precipitate at pH values close to their isoelectric point. This property can be used to selectively precipitate different proteins from solution. As most food proteins have their isoelectric point in the range pH 4-5, this pH range is frequently used for protein recovery in the food processing industry. Typically, after alkaline, acid or salt extraction, the pH of the protein extract is adjusted to the desired isoelectric point to induce protein precipitation, followed by centrifugation to recover the protein, washing to remove salts, neutralization and drying.

Organic solvents such as acetone and ethanol can be used to induce protein precipitation. Similar to the salting-out phenomenon, addition of organic solvents removes water from the hydration spheres of the protein allowing electrostatic forces to bring oppositely charged regions of the protein together. Water is, thus, removed both by bulk replacement by the organic solvent and by structuring of the water around the organic molecules. Acetone, ethanol, acetone-methanol, chloroform-methanol, tricholoroacetic acid-ethanol are examples of solvents and solvent mixtures frequently used for protein recipitation. Modifications in protein functionality, safety of solvent handling and miscibility are some of the challenges associated with organic solvent protein precipitation.

Hydrodynamic treatment and cavitation are useful in washing and neutralizing a reactive substance from a protein solution. After recovery, proteins can be further purified by repeated washing with an appropriate solvent followed by centrifugation and/or filtration. This extra unit operation allows the removal of non-protein soluble components trapped within the interstitial spaces of the precipitate. The process can be further optimized to remove contaminating soluble proteins prior to drying (e.g., by selecting an appropriate pH of the water used for washing). For example, washing the acid precipitated soy protein with pH 4.5 wash water, then resolubilizing and washing at pH 9.0 culminating with a final pH 4.5 precipitation, fat content can be further decreased from 7-9% to 3-6%, while increasing the protein content from ~81-85% to ~90-92% without an added washing step.

With reference to the attached drawings, FIGS. 1-7, various embodiments of a device 20 for the creation of cavitation processes in fluid flows resulting in localized regions of increased pressure, heat release and vigorous mixing to generate changes in fluids are disclosed. The method and device include the use of a flow-through hydrodynamic multi-stage cavitation reactor 20 of the type disclosed to promote chemical and physical processes and reactions that occur in a short time and results in new products. Intense localized heat released because of gas compression and microjet formation, which accompany the implosion of cavitation bubbles, excite molecules contained in vapors and in the adjacent layers of surrounding fluid transiently enriched with the high-boiling point ingredient(s), thereby driving chemical reactions and processes.

The device 20 is especially suitable for processing fluids, such as water and organic solvents, cell extracts, biological fluids, emulsions and solutions, biomass suspension, etc. The term "fluid" includes but is not limited to a pure liquid comprised of identical molecules, a homogeneous or heterogeneous fluidic mixture, media liquefied prior to cavitation treatment, two- or multi-phase systems including emulsions and dispersions, solutions, gases and/or other matter dissolved in suitable solvent(s), melted matter, dispersions, suspensions, slurries, liquefied gases, cell culture or broth, biological fluids, tissues, and the mixtures thereof.

The various parts of the apparatus 20 can be fabricated from a STELLITE® alloy, steel, stainless steel, aluminum, copper, brass, silver, zinc, nickel, PTFE, FEP or other fluoropolymers, poly (methyl methacrylate), PEEK, PBAT, PETG, PVC, polycarbonates, acrylic materials, polycrystalline diamond or other finished or unfinished metals and material(s).

Figure 2A:
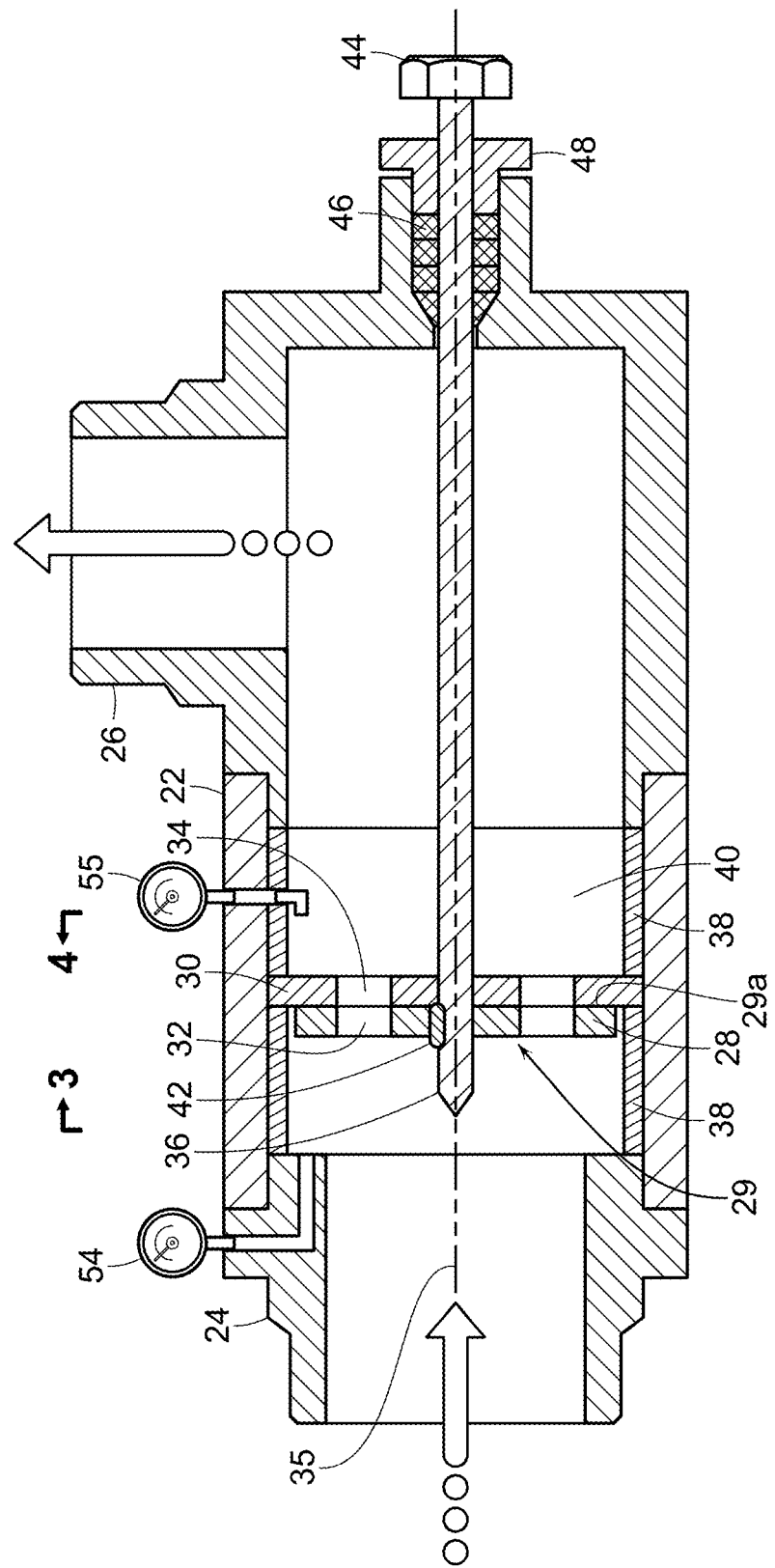
FIG. 2A is a cross-sectional view taken along line 2-2 of FIG. 1.
Figure 2B:
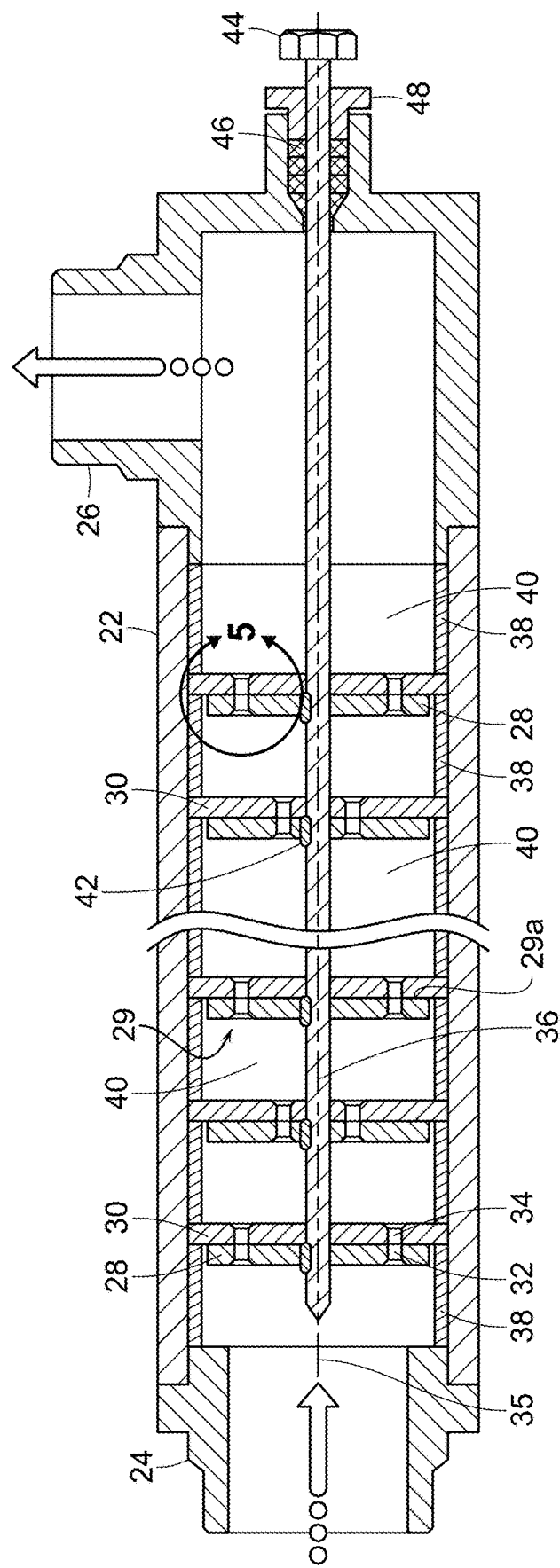
FIG. 2B is a cross-sectional view of an alternate embodiment of the view shown in FIG. 2A.

The apparatus 20 comprises a housing 22 having an inlet pipe 24 and an outlet pipe 26 for connecting in-line with an industrial pipeline (not shown). Housing 22 preferably has a circular cross-section and may be provided with gas inlet port(s) 25. Inside housing 22 there is at least one variable multi-jet nozzle 29 (FIG. 2A) or a plurality of variable multi-jet nozzles 29 (FIG. 2B). A variable multi-jet nozzle 29 consists of two disks 28 and 30, in which there are multiple through channels 32 and 34.

Variable multi-jet nozzles 29 generate vortexes in fluid flow and intensive turbulent flow, thus creating microvortexes with locally decreased pressure which is equivalent to the pressure of heavy vapors of the processed fluid under the given temperature. When pressure in the local area is reduced to the pressure of heavy vapor, micro-bubbles or the so-called cavitation nuclei begin to grow. Micro-bubbles grow in size and turn into cavitation bubbles, which pulsate and collapse in the area of increased pressure. In order to create the conditions for pulsation and collapse of cavitation bubbles the flow-through cavitation device has working chambers. The flow-through cavitation generator contemplates sequential combination of cavitation zones—multi-jet nozzles as well as zones of increased pressure for cavitation bubbles collapse and pulsation—working chambers. The number of stages "cavitation bubbles generation zone—cavitation bubbles collapse zone" is determined by the degree of technological effect per one flow of processed fluid through flow-through cavitation generator. The minimum number of stages of cavitation bubbles generation and collapse at least 1, but the maximum number can be theoretically unlimited, but it can practically reach be as many as 10-12 stages.

The number of variable multi-jet nozzles 29 is determined by the number of working areas for the hydrodynamic and cavitation effects on the fluid required to achieve the desired technological effect during processing of the liquid flow. For a particular process and the processed fluid with certain parameters, the number of working areas and, respectively, the number of consecutive variable multi-jet nozzles 29, is determined empirically.

The first disk 28 of a variable multi jet nozzle 29 along the fluid flow is rotatable about the central axis 35 of the apparatus 20. The second disk 30 of a variable multi jet nozzle 29 along the fluid flow, abuts against the first disk 28 along plane of contact 29a and is fixed, e.g., stationary within the apparatus 20. Fixation of stationary disks 30 is accomplished by bushings 38. Each stationary disk 30 is followed by working chamber 40 bounded by the walls of bushing 38, the preceding stationary disk 30 and subsequent movable disk 28, if any. The working chamber 40 located after stationary disk 30, which is the last along the flow, is bounded by the inner walls of the bushing 38 and the walls of outlet 26.

A shaft 36 extends along the central axis 35 through central openings of disks 28 and 30. Movable disks 28 are fixed to the shaft 36 by pin key 42 and rotate with the same. Rotation of the shaft 36 is carried out by rotation—manual or motorized—of shaft head 44. Shaft 36 passes through stationary disks 30 so as to allow free rotation of the shaft 36 relative to the disk 30. The shaft outlet is sealed by stuffing box 46, pressed by closing sleeve 48. Rotation of shaft 36 can be carried out manually or by using a special servomotor as described below.

Figure 3A:
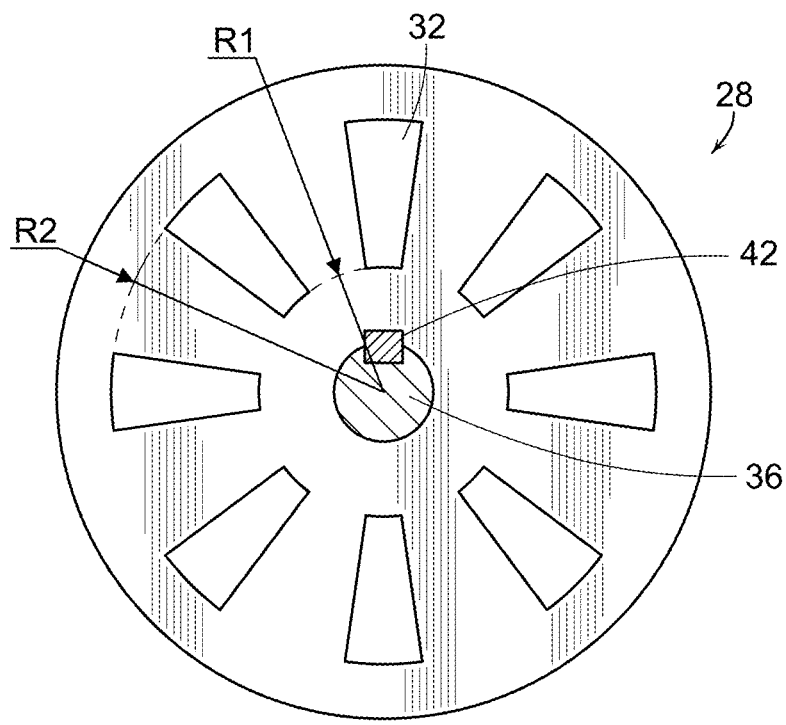
FIG. 3A is a cross-sectional view of the movable disk taken along line 3-3 of FIG. 2A.

The number, shape and arrangement of channels 32 and 34 through disks 28 and 30 may have different embodiments. The cross section of the channels may have a shape of the angular sector bounded on one side by radial lines and radii $R_n$ and $R_{n+1}$ (n=1, 3, 5, . . . - odd numbers) that are equidistant from the central axis of the disk for each channel. In FIGS. 3A-4, the odd numbers represent the side of the angular sector closest to the central axis 35. FIGS. 3A-3D show four embodiments of channels 32 in movable disk 28. FIG. 4 only illustrates one embodiment of channels 34 in stationary disk 30 for convenience. The channels 34 of stationary disk 30 may have a shape and configuration in various forms similar to that shown and described for movable disk 28 in FIGS. 3A-3D.

Figure 3B:
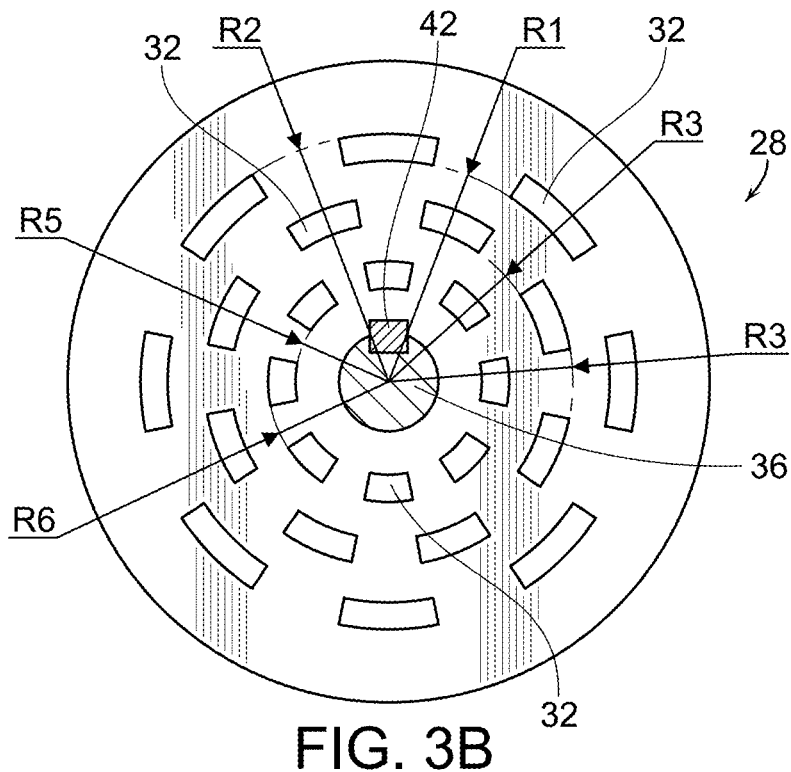
FIG. 3B is a cross-sectional view of an alternate embodiment of the movable disk taken along line 3-3 of FIG. 2A.
Figure 3C:
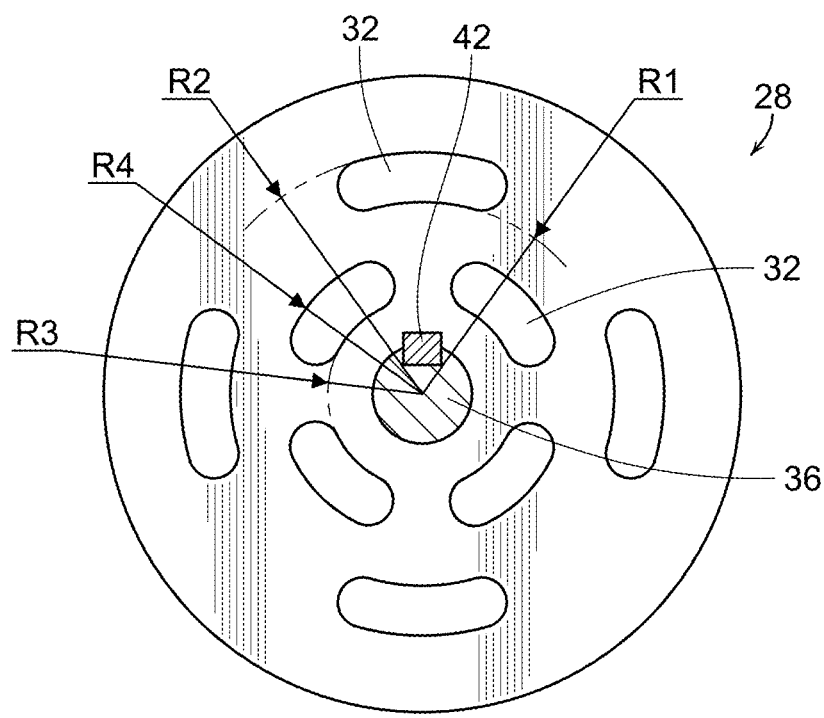
FIG. 3C is a cross-sectional view of an alternate embodiment of the movable disk taken along line 3-3 of FIG. 2A.
Figure 4:
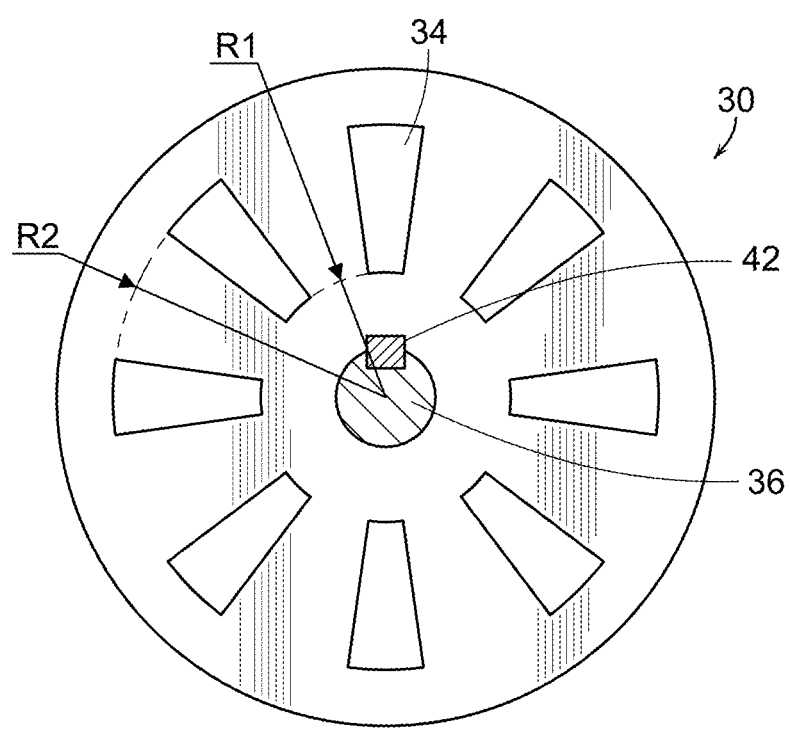
FIG. 4 is a cross-sectional view of the stationary disk taken along line 4-4 of FIG. 2A.

Channels that have cross-sections in the shape of angular sectors bounded by radii $R_n$ and $R_{n+1}$ can be located at different distances from the central axis of the disk (FIG. 3B). Lateral lines of angular cross-sectional sectors of the channels can be shaped as semicircles (as shown in FIG. 3C), acute-angled, or any other shape. The number of channels limited by pairs of radii $R_n$ and $R_{n+1}$ can range from one to thirty-six or more, and it is determined by the geometrical dimensions of disks and pressure values and the fluid flow rate in the channels to create intensive cavitation. Radii $R_n$ and $R_{n+1}$ are determined in the plane of contact 29a of disks 28 and 30.

Figure 3D:
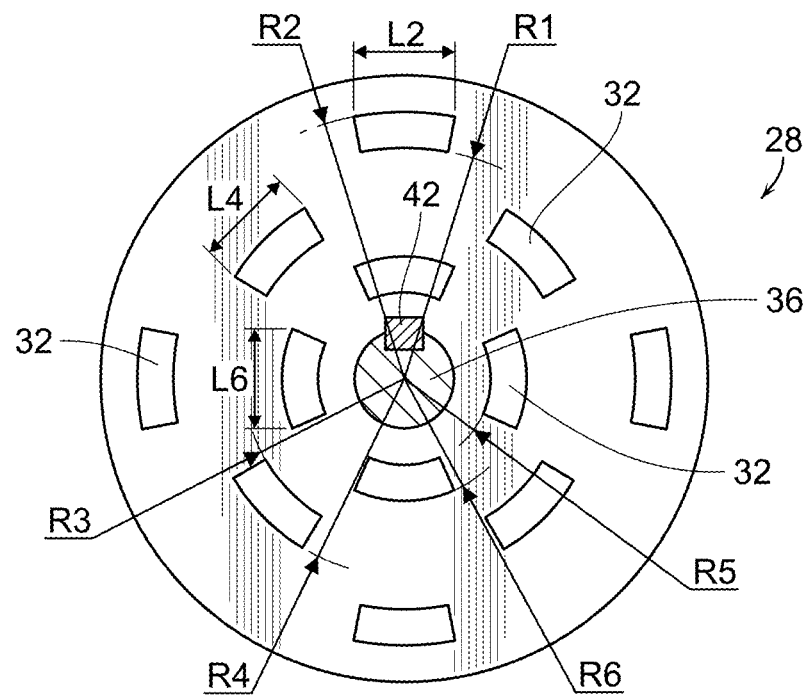
FIG. 3D is a cross-sectional view of an alternate embodiment of the movable disk taken along line 3-3 of FIG. 2A.

The ratio of the radii determining the size of one row of channels 32, 34 located on the same row can have the ratio $1.1 \leq R_{n+1}/R_n \leq 10$. The lengths of arcs $L_{n+1}$, on radii $R_{n+1}$, determining the size of the cross section of channels can have the ratio $0.5 \leq L_{n+1}/L_{n+3} \leq 5$ (as shown in FIG. 3D). The number of rows with radii $R_n$ and $R_{n+1}$, along which channels 32, 34 are located in the disks 28, 30, can reach one to ten and more, and they are determined by the geometric size of the disk, the pressure and the fluid flow rate in the channels 32, 34 to create intensive cavitation. While FIG. 4 only shows an embodiment of stationary disk 30 with channels similar in shape and configuration to those of movable disk 28 shown in FIG. 3A, a person skilled in the art will realize that the stationary disk 30 preferably has channels 34 that match the shape and configuration of the channels 32 in the movable disk 28 such as shown in FIGS. 3B-3D, or any other shape.

Figure 5A:
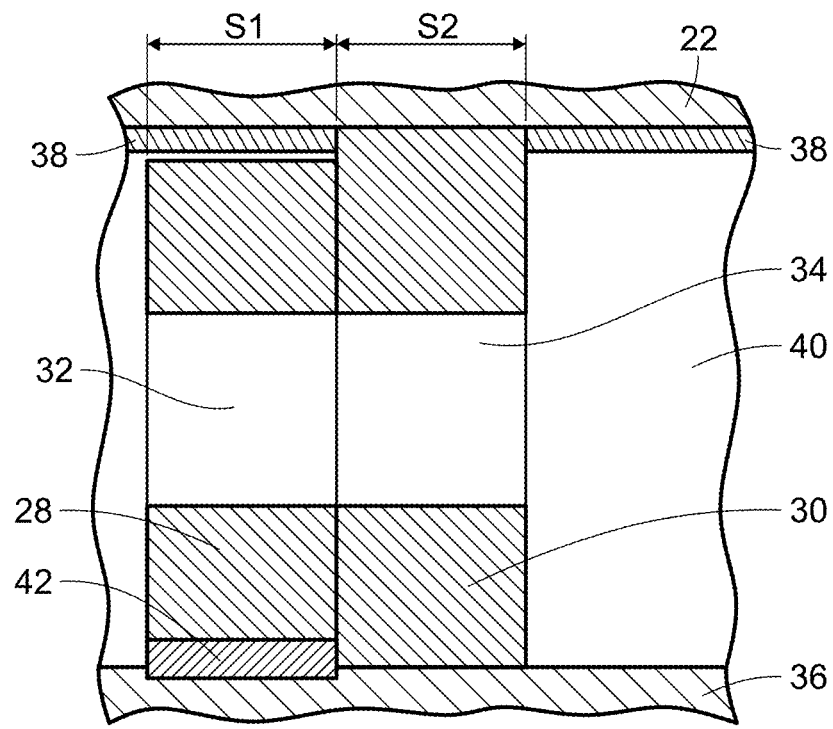
FIG. 5A is a longitudinal section of disks constituting a multi-jet nozzle indicated by circle 5 of FIG. 2B.
Figure 5B:
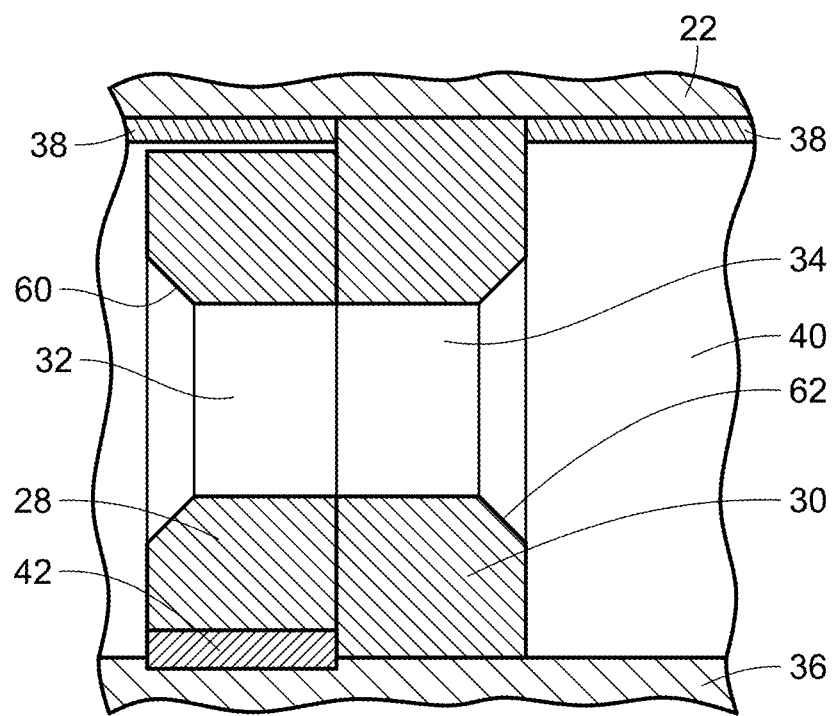
FIG. 5B is a longitudinal section of an alternate embodiment of disks constituting a multi-jet nozzle indicated by circle 5 of FIG. 2B.
Figure 5C:
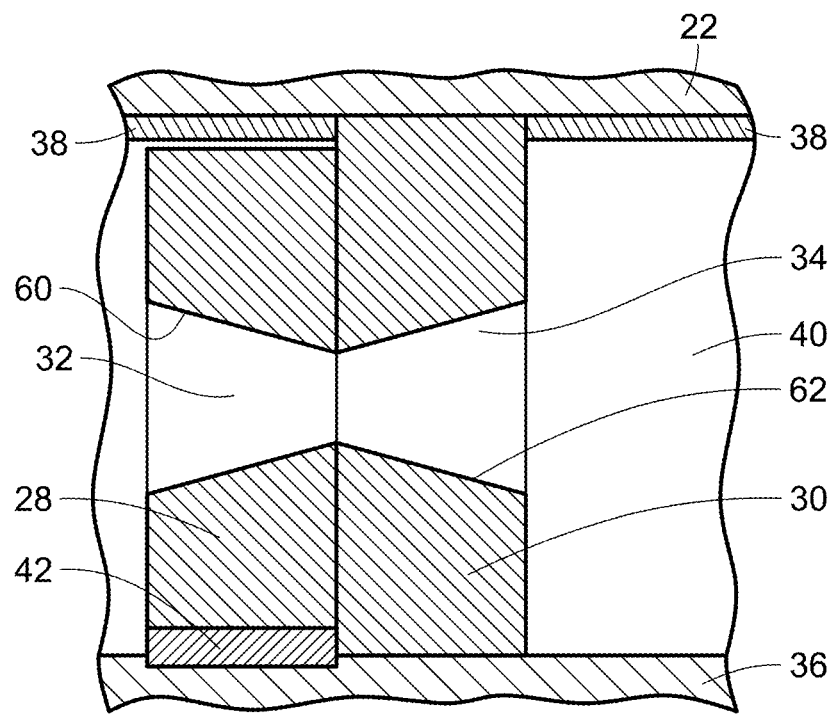
FIG. 5C is a longitudinal section of an alternate embodiment of disks constituting a multi-jet nozzle indicated by circle 5 of FIG. 2B.
Figure 5D:
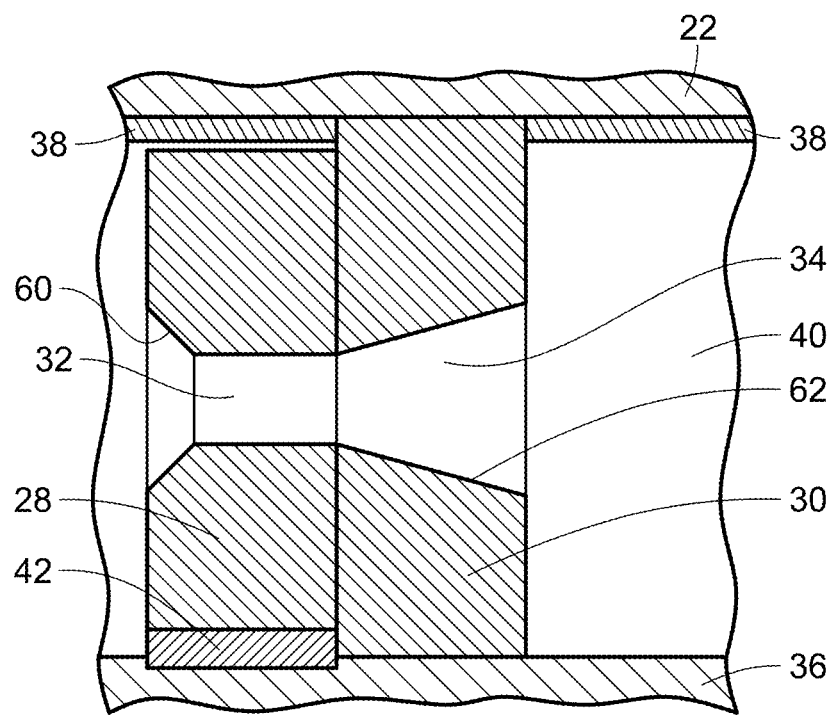
FIG. 5D is a longitudinal section of an alternate embodiment of disks constituting a multi-jet nozzle indicated by circle 5 of FIG. 2B.

The longitudinal section of channels 32 and 34 can be rectangular (FIG. 5A), have partial and/or complete shape of a converging cone 60 in the channels 32 of movable disk 28, and the shape of diffuser 62 in channels 34 of stationary disc 30 (FIG. 5B, 5C). The shape of the longitudinal section in channel 32 of movable disk 28 and channels 34 of stationary disc 30 may have a cross section in the shape of Venturi tube (FIG. 5D). The ratio of the lengths S1 and S2 of channels 32 and 34 may be in the range of $1 \leq S2/S1 \leq 10$.

Each variable multi jet nozzle 29 can have different variations in shape, position and size of the flow cross section area of channels 32 and 34 in disks 28 and 30. The number, shape, arrangement and size of flow area of channels 32, 34 of each variable multi jet nozzle 29 are selected depending on the characteristics of the processed liquid, the process parameters and calculated values of the hydrodynamic cavitation, which should be as small as possible.

The device 20 works as follows: fluid is fed by a pump or similar mechanism in inlet pipe 24 and moves through channels 32 of movable disk 28 and channels 34 of stationary disk 30, which are elements of the variable multi-jet nozzles 29. When fluid goes through the channel 32 and then through immediately adjacent channel 34 the fluid flow develops vortices, detached flows and cavitations. The above-mentioned effects influence the particles of the emulsion or any other heterogeneous fluid and lead to their intensive dispersion and homogenization, as well as separation of boundary layers on the particles. When cavitating bubbles get into the working chamber 40 in the direction of fluid flow they pulsate and collapse thus producing microscale pulsations and emissions of cumulative jets, as a result, they influence the particles of the processed fluid and the fluid as a whole, intensifying heat and mass transfer processes and destroying the substances.

The bubbles' implosion results in the release of a significant amount of energy that drives reactions and processes and heats the fluid. The size of the bubbles depends on the properties of the fluid, the design of the cavitation device, the pump pressure and other fluid conditions. In practice, the pump pressure is gradually increased until a cavitation field of proper intensity is established. In addition to determining the size, concentration and composition of the bubbles, and, as a consequence, the amount of released energy, the inlet pressure governs the outcome of triggered reactions.

Figure 6A:
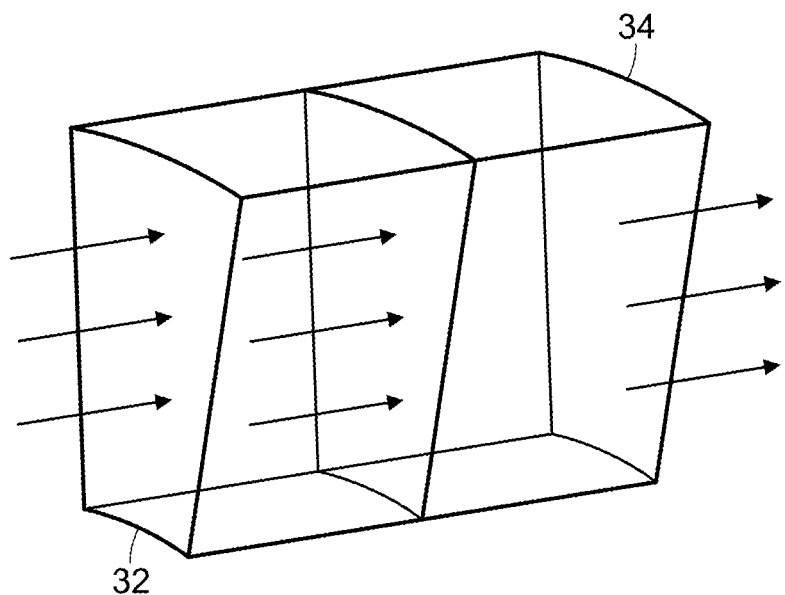
FIG. 6A depicts an arrangement of channels in a multi-jet nozzle.

To control the intensity of hydrodynamic cavitation occurring in the channels 32, 34 of the variable multi-jet nozzles 29, their design allows adjusting the value of their flow cross sectional area. In the initial position channels 32 in movable disks 28 are fully aligned with channels 34 in stationary disks 30 (FIG. 6A). In this position, the channels 32, 34 have the largest flow cross sectional area for fluid flow. An increase in the flow rate in the channels 32, 34 of the variable multi-jet nozzles 29 and an increase the intensity of cavitation, can be achieved by reducing the flow cross sectional area of the channels 32, 34. This is possible due to the rotation of movable disk 28, which rotates when shaft 36 is rotated. Rotation of the shaft 36 is accomplished by turning head 44 of the shaft 36 by hand or with a special servomotor.

Figure 6B:
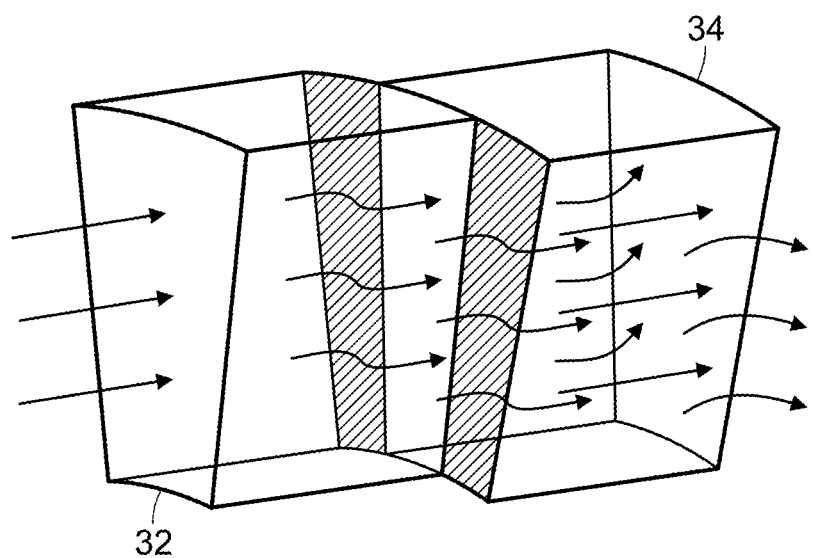
FIG. 6B depicts an alternate arrangement of channels in a multi-jet nozzle.

When rotating disk 28, channels 32 and 34 are no longer fully aligned with the flow cross section profiles and in the plane of contact 29a of disks 28 and 30 the flow cross sectional area of channels 32, 34 of the variable multi-jet nozzles 29 decreases. Part of the fluid flow moving through channel 32 hits the face of disk 30 which partially closes the flow cross section of channel 34 (FIG. 6B). Fluid flow is throttled through the narrower opening formed by the only partially aligned channels 32 and 34 in the contact plane 29a of movable disk 28 and stationary disk 30. Due to this constriction in available flow area, the flow rate increases rapidly and the pressure decreases by the throttling effect, which leads to the formation of vortices and growth of the bubbles of steam and gas, and the development of intensive cavitation.

When passing from channel 32 into channel 34 one part of the fluid flows parallel to the central axis 35, and the other part of the fluid flows at an angle (theoretically from 0 degrees to 90 degrees) to the central axis 35 in the plane of contact 29a of disks 28 and 30 (FIG. 6B). When the fluid flow gets into channel 34, it disperses fan-like from the direction parallel to the central axis 35. Getting into working chamber 40, the flow twists in the opposite direction of rotation of movable disk 28 relative to stationary disk 30. The twisting of the flow causes the intense vortex formation, the emergence of shear flows and the development of cavitation, which intensifies the chemical processes, heat and mass transfer in fluid flow, and dispersion of particles in the flow. The fluid flow passage along the twisted trajectory increases the duration of the fluid presence in the working chamber 40 and hydrodynamic effects (turbulence, cavitation, pressure fluctuations, etc.) on its components.

The intensity of cavitation at any position of the movable disk 28 relative to the stationary disk 30 and the cross section area of channels 32, 34 in the plane of contact 29a of disks 28 and 30 can be determined by calculation or by measurement of the pressure pulsation amplitude using a hydrophone 55 (FIG. 2A) during the collapse of cavitation bubbles. The hydrophone 55 can be placed in the working chamber 40 next to stationary disk 30 at any convenient point. This method of measuring the cavitation intensity is well known and standard.

Figure 7:
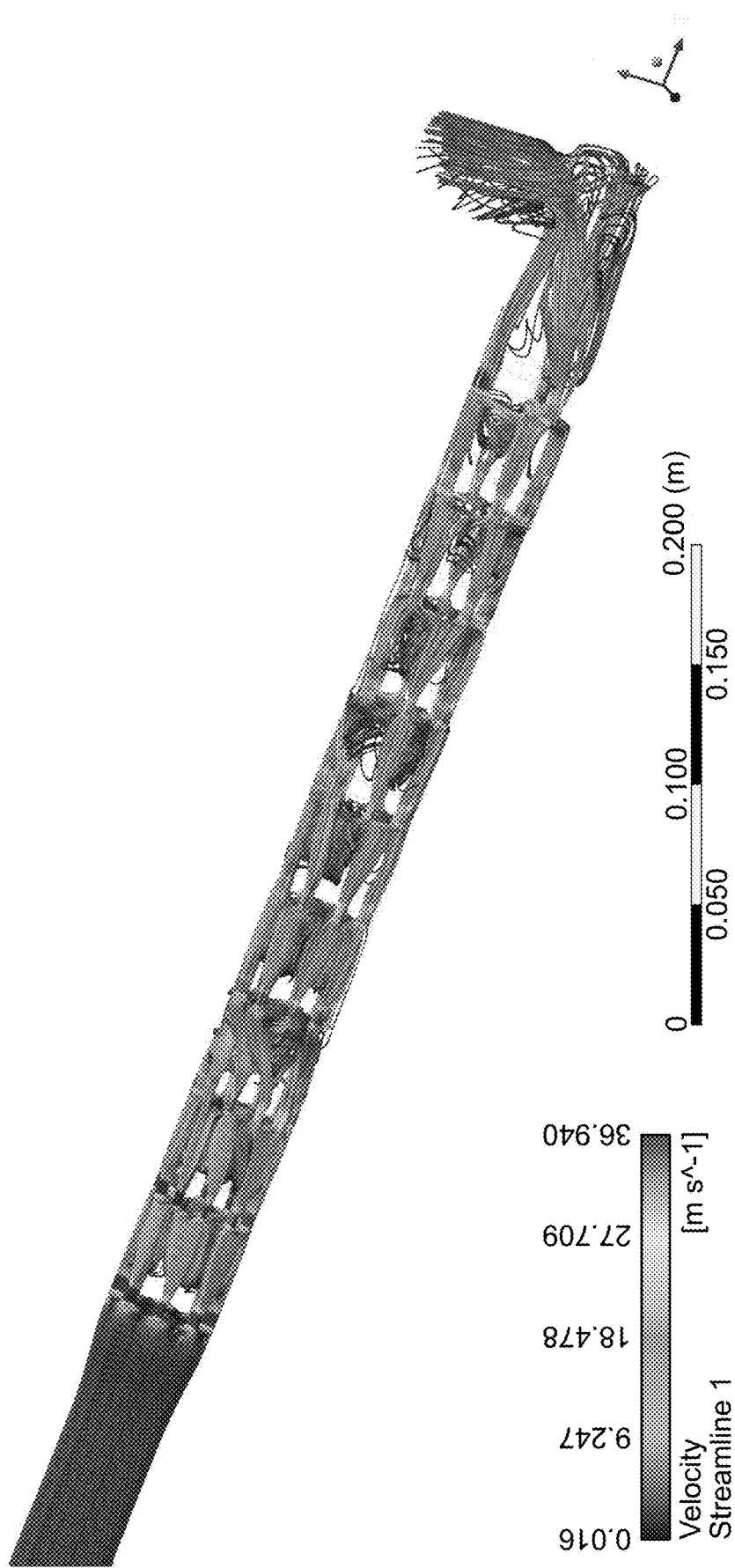
FIG. 7 is a computer model of fluid flow in the device.

The calculation method for determining the degree of development of hydrodynamic cavitation is based on calculating the cavitation number for fixed positions of stationary and movable disks 28 and 30, channels 32 and 34 relative to each other. The starting position is the position of disks 28 and 30 at fully aligned channels 32 and 34. When rotating shaft 36 by a certain amount in degrees, the calculation of fluid flow parameters is carried out in a device by computer simulation, and the number of hydrodynamic cavitation is determined. An illustration of the calculation by this method for one embodiment is shown in FIG. 7. FIG. 7 shows the fluid flow line in the proposed device with the adjustable flow cross section of variable multi-jet nozzles 29.

The design of the device 20 with adjustable flow cross section of variable multi-jet nozzles 29 also allows maintaining the desired flow rate and the intensity of hydrodynamic cavitation by reducing pressure and flowing rate of the processed fluid. When reducing the pressure and flow rate at the inlet 24 of the device 20, the rate in the active zones also decreases. To maintain the processing intensity at the desired level, it is necessary to increase the flow rate. In this case, shaft 36 is rotated, which in turn rotates disk 28 relative to disk 30 so that the available flow area of variable multi-jet nozzles 29 decreases due to displacement of channel 32 overlapped by the face of stationary disk 30. In this way the hydraulic resistance of the variable multi-jet nozzles 29 increases, and so does the pressure at the inlet 24 of the device 20, thereby increasing the flow rate in the fluid flow zone from channel 32 into channel 34 and intensity of hydrodynamic and cavitation processing of fluid.

The shape of the flow cross section of channels 28 and 30 in the plane of contact 29a of disks 28 and 30 significantly influences the regularity of change of the flow area of the variable multi-jet nozzles 29. For large values of radii ratios $R_{n+1}/R_n$ and small values of arc length $L_{n+1}$, the flow cross section area of the variable multi-jet nozzles 29 varies considerably by turning shaft 36 at a certain angle. For small values of radii ratios $R_{n+1}/R_n$ and large values of arc length $L_{n+1}$ the flow cross section area of the variable multi-jet nozzles 29 varies insignificantly by turning shaft 36 at a certain angle.

When the number of variable multi-jet nozzles 29 with adjustable flow section is more than one, each variable multi-jet nozzle 29 may have a different number of channels 32 and 34 of its constituent disks 28 and 30. In a separate variable multi-jet nozzle 29 the shape of channels 32 and 34 (longitudinal and/or cross-sectional), their location along the end faces of disks 28 and 30 of variable multi-jet nozzles 29, the flow cross section area of each variable multi-jet nozzle 29 may vary. Patterns of change in flow cross section area of each variable multi-jet nozzle 29 may also be different. For example, in the first variable multi-jet nozzle 29 when rotating the movable disk 28 the flow area may vary by 50%. In the second variable multi-jet nozzle 29 it may change by 45%, and in the third variable multi-jet nozzle 29 it may change by 30%, and so on. Such varying change may occur at the same degree angle of rotation of shaft 36 and the rotation of movable disks 28 of each variable multi-jet nozzle 29.

Figure 8:
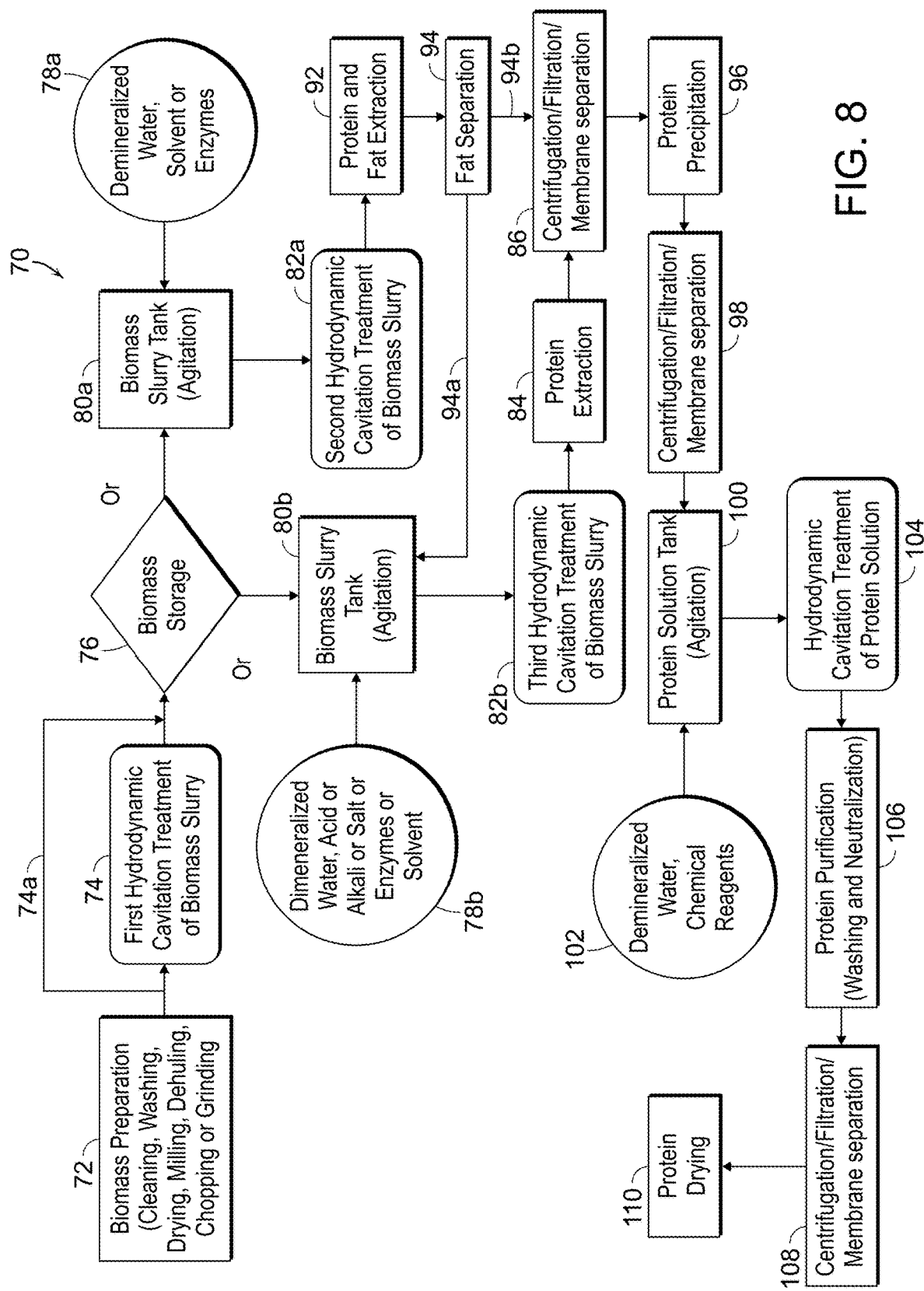
FIG. 8 is a flowchart illustrating the inventive processes for extracting plant protein from biomass.

The device 20 presented in FIGS. 1-7 is used for carrying out the process for extracting protein from biomass, according to the present invention. FIG. 8 illustrates a flowchart of the inventive processes for extracting protein from biomass. The process 70 begins with the step of first biomass preparation 72. Traditionally, protein is produced following either dry or wet milling processes. The first biomass preparation 72 includes cleaning, washing, drying, milling, dehuling, chopping and/or grinding the biomass material to remove unwanted contaminants and reduce its particle size. Typical biomass materials include beans, oilseeds, cereals, hemp, potatoes, camellia, pennies, alfalfa, amaranth, kiwi seeds, nuts, rice, soybeans, and bran.

Preparation 72 using conventional dry grinding processes typically involves the separation of unwanted parts, that is, roots, etc., and then crushing or grinding the wanted parts into small pieces. Preparation 72 may also include washing and drying before grinding, but this requires additional costs and is usually not performed for dry milling. The desired size of the biomass pieces is usually from 1 mm to 5 mm.

Preparation 72 using wet grinding processes may include rinsing with water and drying. With wet grinding for dispersion and splitting of plant fibers and biomass is preferably supplemented with a preliminary or first hydrodynamic cavitation treatment 74 using the apparatus 20. The hydrodynamic cavitation assists in dispersion and splitting of plant fibers. The prepared biomass is then stored in a hopper or similar container 76 until it is ready for further processing. Whether wet or dry milling, the first hydrodynamic cavitation treatment 74 may be bypassed 74a.

As illustrated in FIG. 8, the wet milling process 72 can be carried out as a preparatory stage. Pretreatment for wet grinding (both mechanical and hydrodynamic cavitation) can be used as a preliminary or main extraction of protein from plant biomass.

If the protein is extracted from raw materials containing a large amount of lipids, such as soybeans, then they are preferably extracted from the biomass simultaneously with the protein and then removed from the emulsion, leaving the protein solution for further processing. In the case of high-lipid content, the prepared plant material from the storage tank 76 is mixed with purified water and/or fat solvent or enzymes (for example, lipase, cellulase) 78a in the tank 80a and then subjected to an intermediate or second hydrodynamic treatment 82a.

Intensive hydrodynamic cavitation effects on biomass particles contributes to the destruction of cell tissues, fiber fluffing, deep penetration of the extractant and enzymes into the pores and capillaries of plant material particles. This intensifies the process of mass transfer or extraction 92 of lipids and protein from the plant material as an emulsion into the main extractant flow. Enzymes damage and/or destroy the cell walls of plants by increasing the permeability of oil in oil seeds. The emulsion containing biomass particles, lipid complexes and protein is separated 94, as in a centrifuge, into solid waste flow 94a and a fat fraction and protein flow 94b. This fat fraction and protein flow 94b is further separated using centrifuging, pressing or membrane equipment 86. If there is still protein in the plant material solid waste flow 94a, it is sent to tank 80b for its further extraction using chemical reagents.

To increase the yield of protein from the biomass solid waste flow 94a, chemical and biological reagents may be added: acids, alkalis, salts, solvents, enzymes, which come together with demineralized water or as a separate liquid component 78b from component dosing systems. The components of the extractant in predetermined proportions are sent to the container 80b to create a homogeneous suspension of biomass. The amount of chemical and biological reagents needed for protein extraction is effectively reduced by further hydrodynamic cavitation treatment 82b of the biomass suspension.

The premixed biomass suspension from tank 80b is pumped under pressure to the multi-stage cavitation device for the third hydrodynamic cavitation treatment 82b. Intense hydrodynamic and cavitation effects on biomass particles contribute to the destruction of cell tissues, fiber loosening, deep penetration of the extractant into the pores and capillaries of plant material particles, intensifies the process of solubilization and mass transfer of protein 84 from plant material into the main extractant flow.

The biomass suspension after the third hydrodynamic cavitation treatment 82b and the protein extraction process 84 goes to the previously described separation of the suspension by centrifugation and/or filtration or membrane separation 86. The choice of technology and equipment for separating the plant mass from the liquid protein solution depends on the concentration and size of the plant particles, productivity, requirements for solution purity and other process parameters. Membrane equipment can be either flexible or rigid (ceramic) membranes.

After separation of the vegetable meal, the protein is separated from the solution by precipitation 96. Most proteins precipitate at pH values close to their isoelectric point. This property can be used to selectively precipitate different proteins from solution. As most food proteins have their isoelectric point in the range pH 4-5, this pH range is frequently used for protein recovery in the food processing industry. Typically, after alkaline, acid or salt extraction, the pH of the protein extract is adjusted to the desired isoelectric point to induce protein precipitation, followed by centrifugation to recover the protein. Other methods of protein precipitation are also used in industry. The precipitated protein is separated from the solution by centrifugation or pressing or membrane separation 98.

After recovery, proteins can be further purified by repeated washing with an appropriate solvent followed by centrifugation and/or filtration or membrane separation. This extra unit operation allows the removal of non-protein soluble components trapped within the interstitial spaces of the precipitate. The process can be further optimized to remove contaminating soluble proteins prior to drying (e.g., by selecting an appropriate pH of the water used for washing). For this, the concentrated protein enters the tank 100, into which demineralized water is added, as well as, if necessary, chemical reagents 102 (for example, alkalis or acids to obtain the required pH value). To intensify the washing process, the protein solution from the tank 100 is sent to a multi-stage cavitation device for a further or fourth hydrodynamic cavitation treatment 104. Intense turbulence and cavitation in micro-volumes of the solution facilitate subsequent washing and neutralization 106 of the protein from chemicals and oil remaining in the protein.

After this washing and neutralizing the solution, the protein is recovered by centrifugation or pressing or membrane separation 108. Hydrodynamic and cavitation treatment of the biomass suspension and protein solution ensures a long service life of the filtration membranes due to homogenization and fine grinding of particles. The concentrated washed protein solution is then sent to dryer 110. Three techniques most commonly used are freeze drying (lyophilization), spray drying or drum drying.

The first 74, second 82a, and third 82b hydrodynamic cavitation treatment of biomass suspension and later hydrodynamic cavitation treatment 104 of the protein solution can be performed sequentially with the implementation of each treatment or can be applied selectively depending on the type of plant material and process conditions.

In accordance with the present invention, the fluidic reaction mixture is treated either continuously or periodically, by passing through any of the cavitation devices disclosed herein. The devices can be placed anywhere in a production site or any other body. Another design exists in which the device may be fixed in position or movable. In addition, multiple devices may be combined in a series or parallel configuration. In practice, it is necessary to take into account the cost of the device, its production capacity and the energy, maintenance and operation cost. It should be emphasized, that an operator of the hydrodynamic cavitation device is not required to wear high performance safety products for hearing protection, such as earmuffs or earplugs, as would be in the case of high-frequency cavitation.

Hydrodynamic cavitation is essentially generated by a change in bulk pressure in a liquid flow by variation of the velocity of the flow through well-defined geometries. In the simplest situation, hydrodynamic cavitation can be generated by forcing or throttling high pressure discharge from a pump through constrictions such as a venturi or an orifice. In this case, the velocity of the flow increases with reducing flow area causing a concurrent reduction in bulk pressure. If the throttling is sufficient, the pressure in the flow in the region downstream of the constriction may actually fall to or below the vapor pressure of the medium. This causes the release of dissolved gas in the medium or generation of vapor bubbles in the liquid medium. These bubbles undergo oscillation with a recovery of pressure in the region further downstream resulting in a final transient collapse. The oscillations of the bubbles generate intense microturbulence in the medium causing vigorous mixing.

For a heterogeneous reaction system, this turbulence can create homogenic slurries between phases generating high interfacial area that can enhance the mass transfer and the reaction kinetics. Cavitation can occur at numerous locations in a fluid body simultaneously and can generate very high localized pressure and temperature. At the transient collapse of the bubble, the temperature and pressure in the bubble can reach extremely high values (~3000 K, ~100 bar or even higher) that can cause decomposition of the solvent vapor entrapped in the bubble resulting in the generation of extremely reactive radicals that can accelerate the kinetics of a chemical process.

Cavitation also results in the generation of localized turbulence and liquid micro-circulation, enhancing mass transfer. Thus, mass transfer-limited reactions, endothermic reactions and reactions requiring extreme conditions can be effectively carried out using cavitation.

The flow essentially undergoes a sudden contraction and expansion that generates essential pressure variation for the in-situ generation and collapse of either vapor or gas bubbles. As stated earlier, these bubbles undergo volume oscillations and a transient collapse, which can create cavitation effects by intense energy concentration that results in extremes of temperature and pressure and also intense convection due to micro-turbulence and shock waves. However, this effect is seen either inside the bubble (of initial size ~50-100 microns, which is compressed to about $1/10^{th}$ of its initial size) or in the bulk liquid in close proximity to the bubble. Thus, the energy concentration created by transient bubbles is on an extremely small spatial and temporal scale.

Through these contractions and expansions, the flow may get separated from the walls of the conduit. In this case, there is significant loss in the pressure head of the flow, which is manifested in terms of generation of turbulence in the flow. The turbulence creates fluctuations in the bulk pressure at low frequencies (1 to 2 kHz). These turbulent fluctuations are essentially superimposed over the mean pressure of the flow that keeps on increasing with the expansion of the flow. These fluctuations alter the behavior or pattern of radial motion of the cavitation bubble. In this case, the bubble undergoes an explosive growth followed by a transient implosive collapse. The cavitation effect produced by these bubbles is several folds higher than the bubbles in simple ventures. The difference in the cavitation bubble behavior in a orifice flow and in a venturi flow has been studied at length. (VS Moholkar and AB Pandit, Chemical Engineering Science, 2001).

In order to intensify solid-to-liquid extraction of a protein it is necessary to ensure that liquid penetrates into the pores of a solid body and is removed from the particle surface. In heterogeneous mass transfer, cavitation bubbles collapsing at or near the phasic interface causes vigorous mixing. Hydrodynamic flow pulsations, and cavitation increase the yield of protein due to an increase in the surface of contact between the phases, deep penetration of the solvent into the particle pores of biomass.

TABLE 1

Comparison of energy efficiency for different methods.

| Method | Time, min | Yield, % | Yield/energy, $kJ^{-1}$ |
| --- | --- | --- | --- |
| Acoustic | 10 | 99 | $8.6 \times 10^{-5}$ |
| Conventional with stirring | 180 | 98 | $2.7 \times 10^{-5}$ |
| Presented flow-through | 8 | 99.9 | $2.6 \times 10^{-3}$ |

It can be seen from Table 1 that mass transfer processes that take place in a flow-through cavitation generator are correspondingly about 30 times and 100 times more efficient compared to acoustic cavitation or conventional agitation/heating/refluxing methods.

The cavitation devices are effectively static, i.e., contain no moving parts during flow-through processing, and are configured for operation at a set fluid velocity and pressure of fluid medium. As described below, the changing of chamber diameters and surface features within the devices causes the generation of cavitation fluid features, i.e., bubbles. The subsequent collapse of the cavitation bubbles results in the localized elevations of pressure and temperature and drives the extraction process at a higher rate to achieve a higher yield than other processes.

When fluid is subjected to consecutive multi-stage cavitations it is heated up and becomes enriched with bubble nuclei. This lowers the downstream cavitation threshold, intensifies processing and allows selective chemical reactions to occur while targeting compounds of interest. This makes the present device unique and especially suitable for treatment of multi-component fluids such as, for example, mixtures of biomass with water, acids or bases.

The flow-through cavitation devices are preferably multi-stage apparatuses whereby components are manipulated through localized high pressure and temperature impulses and advanced gas phase to solid/liquid phase transfer principles. Hydrodynamic cavitation assumes formation of vapor bubbles within a fluid accelerated to a proper velocity. In practice, cavitation is achieved by forcing fluids into the flow-through hydrodynamic cavitation device accelerated with a high-pressure pump and/or by reducing the available flow cross-sectional area at constant pressure. The faster the flow rate, the lower the cavitation number. A lower cavitation number (especially cavitation numbers less than 1) equates to a higher degree of cavitation. The preferred embodiment of the present invention optimizes the cavitation to achieve the high protein yield by applying the most suitable pump pressure selected from a preferred range of 50-1,500 psi. If too much energy is applied or the treatment time is too long, then the cost goes up. By applying hydrodynamic cavitation at a pump pressure designed for the desired mass transfer and chemical transformation in the entire liquid reaction mixture, the appropriate changes occur and the desired result is achieved.

The present invention uses energy released upon the implosion of cavitation bubbles to carry out mass transfer processes. Hydrodynamic cavitation is the phenomenon of the formation of vapor cavities in a flow of fluid, which is followed by the bubble collapse in a downstream high-pressure zone. In practice, the process is carried out as follows. The fluid flow is pumped into the cavitation device. In a constriction, the flow accelerates causing the pressure to drop. This pressure drop results in the formation of bubbles filled with the vapors of volatile compounds that boil under the given conditions, i.e., a cavitation zone. When the cavitation bubbles move beyond the boundary of the low-pressure zone, the pressure in the flow increases and the bubbles collapse, exposing the vapors found within them and the surrounding liquid layer to localized high pressure and temperature, shearing forces, shock waves, acoustic vibration and electromagnetic irradiation. Each cavitation bubble serves as an independent mini-reactor, in which chemical reactions and/or mass transfers occur, particularly at the vapor/liquid interface. The localized pressure and temperature are significantly higher than those found in many other industrial processes where the overall pressure and/or temperature may be increased rather than on a localized scale. The alteration of fluid composition results from the chemical reactions taking place within the collapsing bubbles and/or in the adjacent layers of fluid.

The phenomenon is named cavitation, because cavities form when the fluid pressure has been reduced to its vapor pressure. The vapor bubbles expand as they move and suddenly collapse, creating a region of high pressure. The occurrence of cavitation bubble implosion is accompanied by the formation of numerous deformed micro bubbles. The pressure and temperature of vapors contained in these bubbles are very high. As fluid enriched with these micro bubbles moves into a reduced pressure zone, the micro bubbles become nuclei, which are less stable than those originally present in the fluid, and expand. The cavitation bubbles developed from these nuclei enhance the cavitation field intensity. The continuous process of bubble multiplication, expansion and implosion lowers the cavitation threshold because cavitation bubbles grow from the vapor nuclei, whose volume is larger than that of the naturally present nuclei. The sudden collapse causes huge local increases in pressure and temperature, as well as strong shear forces, resulting in high-yield intensification of mass transfer. By subjecting the liquid reaction mixture to hydrodynamic cavitation, the target substance molecules are extracted from the plant material.

Implosion of the generated cavities results in the formation of shock waves, high-velocity local jets and heat dissipation, improving both mass transfer and reaction rate. As the cavitation number decreases, fluctuating cavities with periodic vortex shedding and vapor-filled cavities are observed. In the cavitation regions, strong momentum transfer between higher and lower flow layers occurs. The cavitation bubble dimensions and the intensity of the cavitation field increase as the fluid moves through the cavitation device. An increase in the difference in the flow pressures favors cavitation and vortex formation.

From a general point of view, the initial processing of the biomass suspension in the cavitation apparatus takes place at ambient temperature and ambient pressure. No heat is added during cavitation treatment, although preheating may occur. Cavitation enhancement of mass transfer occurs at pump pressures of 50 to 1500 psi, ideally about 500 psi.

It is important to note that the method of the claimed invention is designed to operate in a continuous manner as the fluid flow is pumped through the cavitation device. Most prior art disclosures include cavitation systems that comprise batch or hybrid batch/continuous systems. In such prior art systems, the reagents are introduced to the system and the reaction is allowed to proceed to equilibrium in a residence chamber/vat. Once equilibrium is achieved, a portion of the products are removed from the system so that the remaining reagents and any subsequently added reagents may react to establish a new equilibrium. Such prior art processes require a long residence time, in some cases many hours, in order to produce the desired yield.

This is especially important in extraction processes such as this where the liquid in a solid/liquid interface around a particular area of the biomass may become saturated with protein and prevent the extraction of further proteins until the liquid is changed. The higher the concentration of products, i.e., proteins, the slower the rate of extraction. This makes the prior art methods time consuming, expensive, and less efficient when compared to the claimed method with a comparatively faster extraction process with a high-yield.

The present invention makes it possible to carry out accelerated cavitation-assisted proteins extraction processes by causing the repeated generation and subsequent collapse of cavitation bubbles. The invention also allows for the extraction of proteins without consuming large amounts of energy and avoids high-pressure operations. The present invention can extract proteins and produce protein in a more efficient and more cost effective manner.

The present invention employs a specific process for extracting proteins from biomass using hydrodynamic cavitation in fluids. The process involves flowing a fluidic mixture through the cavitation device having a specified inlet flow velocity and system pressure through acceptable piping and pumping means. The inlet velocity and system pressure vary according to the reaction mixture properties. The preferred flow rate is approximately 50-100 gallons per minute, but may be adjusted lower or higher according to output requirements without affecting the results of the cavitation process. The preferred system pressure is 50-1,500 psi. In a particularly preferred embodiment, the inlet velocity is ten gallons per minute and the system pressure is about 500 psi.

The apparatus and methods described herein, subject to the conditions and specifications of use, provide a method for extracting proteins from biomass and obtaining protein. The treatment depends on the properties of the biomass suspension being processed and the energy requirements required for the formation of cavitation in the liquid.

What is claimed is:

1. A process for extracting proteins from plant biomass, comprising the steps of:
preparing plant biomass for extraction of protein, including cleaning, washing, drying, milling, dehulling, chopping, or grinding raw plant biomass to remove contaminants and reduce particle size;
storing the prepared plant biomass in a storage hopper;
combining the stored plant biomass from the storage hopper with demineralized water, acid, alkali, salt, enzymes, or solvent in an agitation tank forming a biomass slurry;
subjecting the biomass slurry to a hydrodynamic cavitation treatment to extract plant protein from the biomass slurry;
separating the biomass slurry into a protein extract and biomass waste in separation equipment including a centrifuge, a filter press, or a filter membrane;
adjusting a pH value of the protein extract to an isoelectric point for proteins in the plant biomass;
precipitating plant proteins from the protein extract at the isoelectric point; and
separating the plant proteins from the protein extract.

2. The process of claim 1, wherein when the preparing step involves a wet grinding process, further comprising the step of subjecting the prepared plant biomass to a preliminary hydrodynamic cavitation treatment to assist in dispersion and splitting of plant fibers, breaking of cell membranes, and increasing available mass transfer surface of biomass, prior to the step of storing the prepared plant biomass.

3. The process of claim 1, wherein the particle size following the preparing step is less than 5 mm.

4. The process of claim 1, wherein when the raw plant biomass has an oil or fat content greater than 10% w/w, further comprising the steps of:
mixing the stored plant biomass with demineralized water, lipid solvent, or lipid enzymes in a mixing tank forming a lipid-containing biomass slurry;
subjecting the lipid-containing biomass slurry to an intermediate hydrodynamic cavitation treatment for breaking of cell membranes, fiber fluffing, and increasing penetration of solvent or enzymes;
extracting a lipid-protein emulsion from the lipid-containing biomass slurry;
separating the lipid-protein emulsion into a lipid fraction and a protein fraction in the separation equipment
transporting the lipid-containing biomass slurry and the lipid fraction to the agitation tank; and
combining the protein fraction with the protein extract prior to the step of adjusting the pH value.

5. The process of claim 1, further comprising the steps of:
combining the separated plant protein with demineralized water or chemical reagents in a protein agitation tank to form a protein wash mixture;
subjecting the protein wash mixture to an additional hydrodynamic cavitation treatment to wash and neutralize the plant protein;
separating the plant protein from the protein wash mixture using additional separation equipment;
drying the plant protein for food grade protein production.

6. The process of claim 1, wherein the plant protein consists essentially of glycoproteins, lipoproteins, metalloproteins, nucleoproteins, phosphoproteins, chromoproteins or a combination.

7. The process of claim 1, wherein the enzymes consists essentially of lipase enzymes or cellulase enzymes.

8. The process of claim 7, wherein the combining step includes introducing microbes or fungi that produce lipase enzymes or cellulase enzymes to the stored plant biomass.

9. The process of claim 8, wherein the microbes or fungi comprise *Escherichia coli, Saccharomyces cerevisiae, Zymomonas mobilis, Lactobacillus buchneri*, or *Clostridium acetobutylicum*.

10. The process of claim 4, wherein the oil or fat content comprises fatty acids, glycerolipids, glycerophospholipids, sphingolipids, sterols, prenols, saccharolipids, polyketides, or a combination.

11. The process of claim 4, wherein the step of subjecting the biomass slurry to a hydrodynamic cavitation treatment and the step of subjecting the lipid-containing biomass slurry to an intermediate hydrodynamic cavitation treatment comprises pumping the same through a hydrodynamic cavitation device at an inlet pump pressure of 50-1500 psi.

12. The process of claim 4, wherein the step of subjecting the biomass slurry to a hydrodynamic cavitation treatment and the step of subjecting the lipid-containing biomass slurry to an intermediate hydrodynamic cavitation treatment comprises pumping the same through a hydrodynamic cavitation device at least two times.

13. The process of claim 1, wherein the plant biomass consists essentially of beans, oilseeds, cereals, hemp, potatoes, camellia, alfalfa, amaranth, kiwi seeds, nuts, rice, soybeans, bran or a combination.

14. A process for extracting proteins from plant biomass, comprising the steps of:
preparing the plant biomass for extraction by mechanical grinding;
forming a first biomass suspension comprising the prepared plant biomass and water;
subjecting the first biomass suspension to a first hydrodynamic cavitation treatment to disperse biomass particles, separate biomass fibers, and disrupt biomass cell membranes forming a processed biomass;
forming a processed biomass suspension comprising the processed biomass combined with one or more of water, organic solvent, and enzymes;
subjecting the processed biomass suspension to a second hydrodynamic cavitation treatment to extract proteins and lipids from the biomass, forming a biomass dispersion;
separating the biomass dispersion into a biomass solid waste flow and a lipid-protein emulsion;
separating the lipid-protein emulsion into a lipid fraction and a protein fraction;
forming a second biomass suspension containing the biomass solid waste flow combined with one or more of water, acid, alkali, salts, solvent, or enzymes;
subjecting the second biomass suspension to a third hydrodynamic cavitation treatment to extract proteins from the second biomass suspension forming a second protein fraction;
combining the protein fraction and the second protein fraction to form a combined protein fraction;
precipitating proteins out of the combined protein fraction forming a protein solution;
combining the protein solution with one or more of water and reagents forming a prepared protein solution;
subjecting the prepared protein solution to a fourth hydrodynamic cavitation treatment to facilitate separation of proteins from the prepared protein solution;
separating the prepared protein solution into a liquid solution and purified concentrated protein; and
drying the purified concentrated protein.

15. The process of claim 14, wherein the biomass consists essentially of beans, oilseeds, cereals, hemp, potatoes, camellia, alfalfa, amaranth, kiwi seeds, nuts, rice, soybeans, bran or a combination.

16. The process of claim 14, wherein the step of forming the first biomass suspension comprises mixing the prepared plant biomass with demineralized water in a ratio of 10% to 50% w/v.

17. The process of claim 14, in the step of forming the second biomass suspension, wherein the acid consists of citric acid in a range of 1% to 5% v/v or sulfuric acid in a range of 1% to 5% v/v, and the alkali consists of sodium hydroxide in a range of 1% to 5% v/v.

18. The process of claim 14, in the steps of forming the processed biomass suspension and forming the second biomass suspension, wherein the enzymes consist of lipase enzymes or cellulase enzymes.

19. The process of claim 18, wherein the steps of forming the processed biomass suspension and forming the second biomass suspension include introducing microbes or fungi that produce lipase enzymes or cellulase enzymes.

20. The process of claim 19, wherein the microbes or fungi comprise *Escherichia coli, Saccharomyces cerevisiae, Zymomonas mobilis, Lactobacillus buchneri*, or *Clostridium acetobutylicum*, the process further comprising the step of adjusting a pH of the processed biomass suspension and the second biomass suspension to a desired pH for the microbes or fungi.

* * * * *